US010487057B1

(12) United States Patent
Bassaganya-Riera et al.

(10) Patent No.: US 10,487,057 B1
(45) Date of Patent: Nov. 26, 2019

(54) NLRX1 LIGANDS

(71) Applicant: Landos Biopharma, Inc., Blacksburg, VA (US)

(72) Inventors: Josep Bassaganya-Riera, Blacksburg, VA (US); Andrew Leber, Blacksburg, VA (US); Raquel Hontecillas, Blacksburg, VA (US)

(73) Assignee: LANDOS BIOPHARMA, INC., Blacksburg, VA (US)

( * ) Notice: Subject to any disclaimer, the term of this patent is extended or adjusted under 35 U.S.C. 154(b) by 0 days.

(21) Appl. No.: 16/270,350

(22) Filed: Feb. 7, 2019

Related U.S. Application Data

(60) Provisional application No. 62/694,076, filed on Jul. 5, 2018.

(51) Int. Cl.
*C07D 401/14* (2006.01)
*C07D 213/643* (2006.01)
*C07D 213/69* (2006.01)

(52) U.S. Cl.
CPC ....... *C07D 213/643* (2013.01); *C07D 213/69* (2013.01); *C07D 401/14* (2013.01)

(58) Field of Classification Search
CPC .................................................. C07D 401/14
See application file for complete search history.

(56) References Cited

U.S. PATENT DOCUMENTS

| | | | |
|---|---|---|---|
| 8,097,721 | B2 | 1/2012 | Armstrong et al. |
| 8,450,318 | B2 | 5/2013 | Mazik et al. |
| 8,513,420 | B2 | 8/2013 | Mazik |
| 8,637,529 | B2 | 1/2014 | Woller et al. |

FOREIGN PATENT DOCUMENTS

| | | |
|---|---|---|
| CN | 103374025 A | 10/2013 |
| CN | 107789677 A | 3/2018 |
| JP | 2001-354639 A | 12/2001 |
| JP | 2004-250345 A | 9/2004 |
| JP | 2009-096723 A | 5/2009 |
| JP | 2017-171603 A | 9/2017 |
| WO | 2007/147605 A2 | 12/2007 |

OTHER PUBLICATIONS

Y. Li et al., Acta Crystallographica Section E (2008) (Year: 2008).*
L. Wang et al., Organic & Biomolecular Chemistry (Jun. 12, 2018) (Year: 2018).*
M. Fujita et al., 117 Journal of the American Chemical Society, 1649-1650 (1995) (Year: 1995).*
M. Chessa et al., 12 Rapid Communications in Mass Spectrometry, 1533-1537 (1995) (Year: 1995).*
J. Pang et al., 12 Journal of Materials Chemistry , 206-212 (2002) (Year: 2002).*

D. Wang et al., 16 Chemistry—A European Journal, 13053-13057 (2010) (Year: 2010).*
S. Ferrini et al., 32 European Journal of Organic Chemistry (2008) (Year: 2008).*
Abreu, M.T., Toll-like receptor signalling in the intestinal epithelium: how bacterial recognition shapes intestinal function. Nat Rev Immunol, 2010. 10(2): p. 131-44.
Allen, I.C., et al., NLRX1 protein attenuates inflammatory responses to virus infection by interfering with the RIG-I-MAVS signaling pathway and TRAF6 ubiquitin ligase. Immunity, 2011. 34(6): p. 854-65.
Arnoult, D., et al., An N-terminal addressing sequence targets NLRX1 to the mitochondrial matrix. J Cell Sci, 2009. 122 (Pt 17): p. 3161-8.
Baumgart, D.C. and W.J. Sandborn, Crohn's disease. Lancet, 2012. 380(9853): p. 1590-605.
Chemical Abstracts Service: Columbus, OH; CAS Registry/CAPlus Structure Records, (Jun. 11, 2017).
Costford, S.R., et al., Male Mice Lacking NLRX1 Are Partially Protected From High-Fat Diet-Induced Hyperglycemia. J Endocr Soc, 2018. 2(4): p. 336-347.
Coutermarsh-Ott, S., et al., NLRX1 suppresses tumorigenesis and attenuates histiocytic sarcoma through the negative regulation of NF-kappaB signaling. Oncotarget, 2016. 7(22): p. 33096-110.
Davis, B.K., et al., Emerging significance of NLRs in inflammatory bowel disease. Inflamm Bowel Dis, 2014. 20(12): p. 2412-32.
Eitas, T.K., et al., The nucleotide-binding leucine-rich repeat (NLR) family member NLRX1 mediates protection against experimental autoimmune encephalomyelitis and represses macrophage/microglia-induced inflammation. J Biol Chem, 2014. 289(7): p. 4173-9.
Feng, H., et al., NLRX1 promotes immediate IRF1-directed antiviral responses by limiting dsRNA-activated PKR translational inhibition. Nat Immunol, 2017. 18(12): p. 1299-1309.
Finn, O.J., Immuno-oncology: understanding the function and dysfunction of the immune system in cancer. Ann Oncol, 2012. 23 Suppl 8: p. viii6-9.
Guo, H., et al., NLRX1 Sequesters STING to Negatively Regulate the Interferon Response, Thereby Facilitating the Replication of HIV-1 and DNA Viruses. Cell Host Microbe, 2016. 19(4): p. 515-528.
Haarberg, K.M., et al., Orally administered extract from Prunella vulgaris attenuates spontaneous colitis in mdr1a(-/-) mice. World J Gastrointest Pharmacol Ther, 2015. 6(4): p. 223-37.
Hong, M., S.I. Yoon, and I.A. Wilson, Structure and functional characterization of the RNA-binding element of the NLRX1 innate immune modulator. Immunity, 2012. 36(3): p. 337-47.
Jaworska, J., et al., NLRX1 prevents mitochondrial induced apoptosis and enhances macrophage antiviral immunity by interacting with influenza virus PB1-F2 protein. Proc Natl Acad Sci U S A, 2014. 111(20): p. E2110-9.
Kale, S.D., et al., Modulation of Immune Signaling and Metabolism Highlights Host and Fungal Transcriptional Responses in Mouse Models of Invasive Pulmonary Aspergillosis. Sci Rep, 2017. 7(1): p. 17096.

(Continued)

Primary Examiner — Alexander R Pagano
(74) Attorney, Agent, or Firm — Daniel A. Blasiole; Charles S. Sara; DeWitt LLP

(57) ABSTRACT

Provided are compounds that target the nucleotide-binding oligomerization domain, leucine rich repeat containing X1 (NLRX1) pathway. The compounds can be used to treat multiple conditions, including chronic and/or inflammatory gastrointestinal diseases, cancers, and infectious diseases.

1 Claim, 26 Drawing Sheets

(56) References Cited

OTHER PUBLICATIONS

Kang, M.J., et al., Suppression of NLRX1 in chronic obstructive pulmonary disease. J Clin Invest, 2015. 125(6): p. 2458-62.
Kim, J.H., et al., FAS-associated factor-1 positively regulates type I interferon response to RNA virus infection by targeting NLRX1. PLoS Pathog, 2017. 13(5): p. e1006398.
Koblansky, A.A., et al., The Innate Immune Receptor NLRX1 Functions as a Tumor Suppressor by Reducing Colon Tumorigenesis and Key Tumor-Promoting Signals. Cell Rep, 2016. 14(11): p. 2562-75.
Kors, L., et al., Deletion of NLRX1 increases fatty acid metabolism and prevents diet-induced hepatic steatosis and metabolic syndrome. Biochim Biophys Acta, 2018. 1864(5 Pt A): p. 1883-1895.
Leber, A., et al., Activation of LANCL2 by BT-11 Ameliorates IBD by Supporting Regulatory T Cell Stability Through Immunometabolic Mechanisms. Inflammatory Bowel Diseases, vol. 24, Issue 9, Sep. 2018, pp. 1978-1991.
Leber, A., et al., Lanthionine Synthetase C-Like 2 Modulates Immune Responses to Influenza Virus Infection. Front Immunol, 2017. 8: p. 178.
Leber, A., et al., NLRX1 Modulates Immunometabolic Mechanisms Controlling the Host-Gut Microbiota Interactions during Inflammatory Bowel Disease. Front Immunol, 2018. 9: p. 363.
Leber, A., et al., NLRX1 Regulates Effector and Metabolic Functions of CD4+ T Cells. J Immunol, 2017, pp. 2260-2268.
Lei, Y., et al., EGFR-targeted mAb therapy modulates autophagy in head and neck squamous cell carcinoma through NLRX1-TUFM protein complex. Oncogene, 2016. 35(36): p. 4698-707.
Li, H., et al., NLRX1 attenuates apoptosis and inflammatory responses in myocardial ischemia by inhibiting MAVS-dependent NLRP3 inflammasome activation. Mol Immunol, 2016. 76: p. 90-7.
Lu, P., et al., Modeling-Enabled Characterization of Novel NLRX1 Ligands. PLoS One, 2015. 10(12): p. e0145420.
Ma, Z., et al., NLRX1 negatively modulates type I IFN to facilitate KSHV reactivation from latency. PLoS Pathog, 2017. 13(5): p. e1006350.
Moore, C.B., et al., NLRX1 is a regulator of mitochondrial antiviral immunity. Nature, 2008. 451(7178): p. 573-7.
Philipson, C.W., et al., Modeling the Regulatory Mechanisms by Which NLRX1 Modulates Innate Immune Responses to Helicobacter pylori Infection. PLoS One, 2015. 10(9): p. e0137839.
Qin, Y., et al., NLRX1 mediates MAVS degradation to attenuate hepatitis C virus-induced innate immune response through PCBP2. J Virol, 2017, p. e01264-17.
Sartor, R.B., Mechanisms of disease: pathogenesis of Crohn's disease and ulcerative colitis. Nat Clin Pract Gastroenterol Hepatol, 2006. 3(7): p. 390-407.
Schwab, M., et al., Association between the C3435T MDR1 gene polymorphism and susceptibility for ulcerative colitis. Gastroenterology, 2003. 124(1): p. 26-33.
Singh, K., et al., NLRX1 acts as tumor suppressor by regulating TNF-alpha induced apoptosis and metabolism in cancer cells. Biochim Biophys Acta, 2015. 1853(5): p. 1073-86.
Soares, F., et al., The mitochondrial protein NLRX1 controls the balance between extrinsic and intrinsic apoptosis. J Biol Chem, 2014. 289(28): p. 19317-30.
Tattoli, I., et al., NLRX1 Acts as an Epithelial-Intrinsic Tumor Suppressor through the Modulation of TNF-Mediated Proliferation. Cell Rep, 2016. 14(11): p. 2576-86.
Theus, M.H., et al., Loss of NLRX1 Exacerbates Neural Tissue Damage and NF-kappaB Signaling following Brain Injury. J Immunol, 2017. 199(10): p. 3547-3558.
Wang, Y.G., et al., The involvement of NLRX1 and NLRP3 in the development of nonalcoholic steatohepatitis in mice. J Chin Med Assoc, 2013. 76(12): p. 686-92.
International Search Report and Written Opinion issued for corresponding PCT application No. PCT/US2019/040386, dated Sep. 13, 2019.
Schmidt et al., Synthesis of functionalized pyridines by substitution of hetarenium-activated pentachloropyridine with bisnucleophiles, Synthesis, vol. 2006, No. 23, Nov. 2, 2006, pp. 3987-3996.
Motaleb et al., Radioiodination and biological distribution of a new s-triazine derivative for tumor uptake evaluation, Journal of Labeled Compounds and Radiopharmaceuticals, vol. 61, No. 14, Sep. 7, 2018, pp. 1058-1068.
Fatima et al., Synthesis, checmical and biological investigations of new Ru(III) and Se(IV) complexes containing 1,3,5-triazine chelating derivatives, Journal of Molecular Structure, vol. 1179, Nov. 24, 2018, pp. 795-808.

\* cited by examiner

NX-5

NX-8

NX-9

NX-10

NX-13

NX-35

NX-37

NX-38

NX-41

NX-43

NX-44

NX-45

NX-46

NX-48

NX-49

NX-50

| ID | Structure | Affinity (kcal/mol) |
|---|---|---|
| NX-5 | 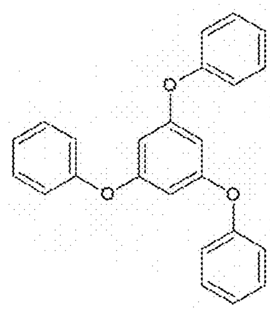 | -8.9 |
| NX-8 | 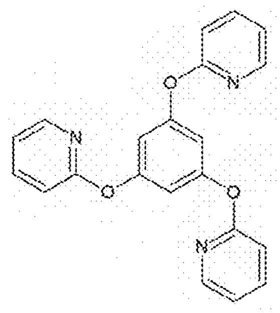 | -9.2 |
| NX-9 | 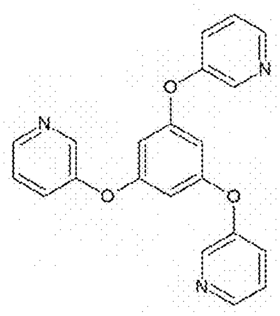 | -9.1 |
| NX-10 | 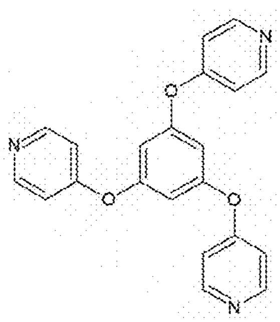 | -9.1 |

| ID | Structure | Affinity (kcal/mol) |
|---|---|---|
| NX-13 | 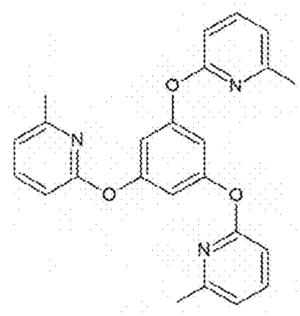 | -10.6 |
| NX-35 | 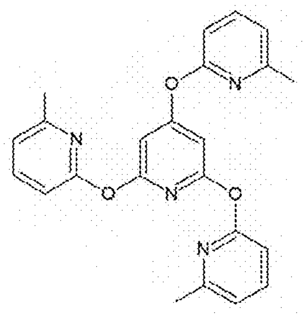 | -10.6 |
| NX-37 | 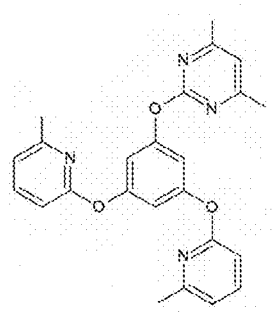 | -11.0 |
| NX-38 | 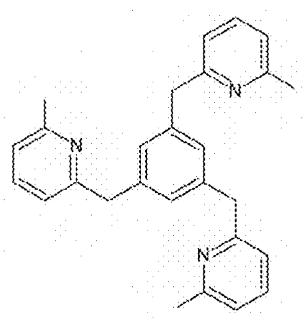 | -9.7 |

FIG. 2B

| ID | Structure | Affinity (kcal/mol) |
|---|---|---|
| NX-41 | 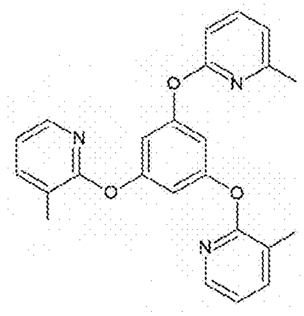 | -11.0 |
| NX-43 | 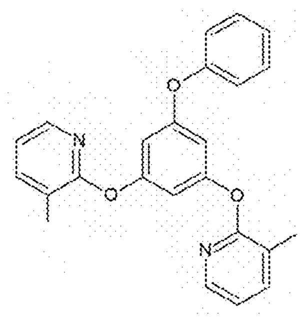 | -11.6 |
| NX-44 | 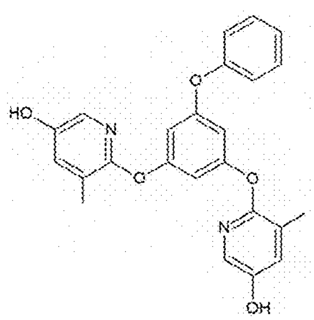 | -11.6 |
| NX-45 | 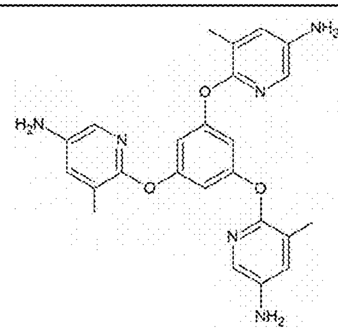 | -10.0 |

FIG. 2C

| ID | Structure | Affinity (kcal/mol) |
|---|---|---|
| NX-46 | 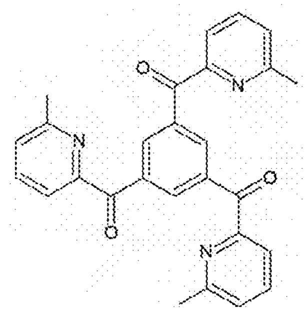 | -10.4 |
| NX-48 | 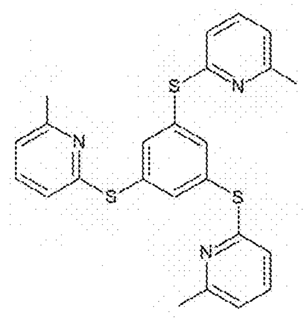 | -10.5 |
| NX-49 | 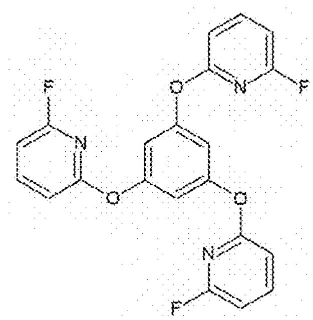 | -10.2 |
| NX-50 | 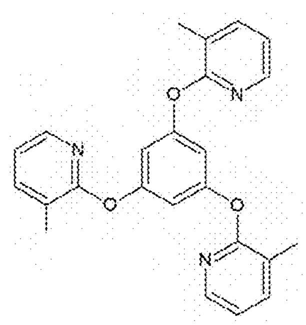 | -11.7 |

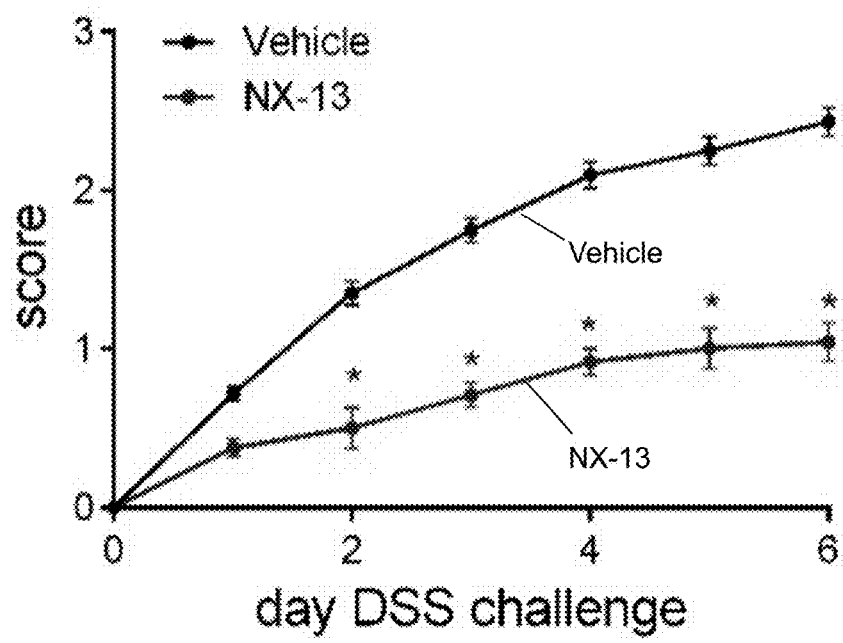
FIG. 7A
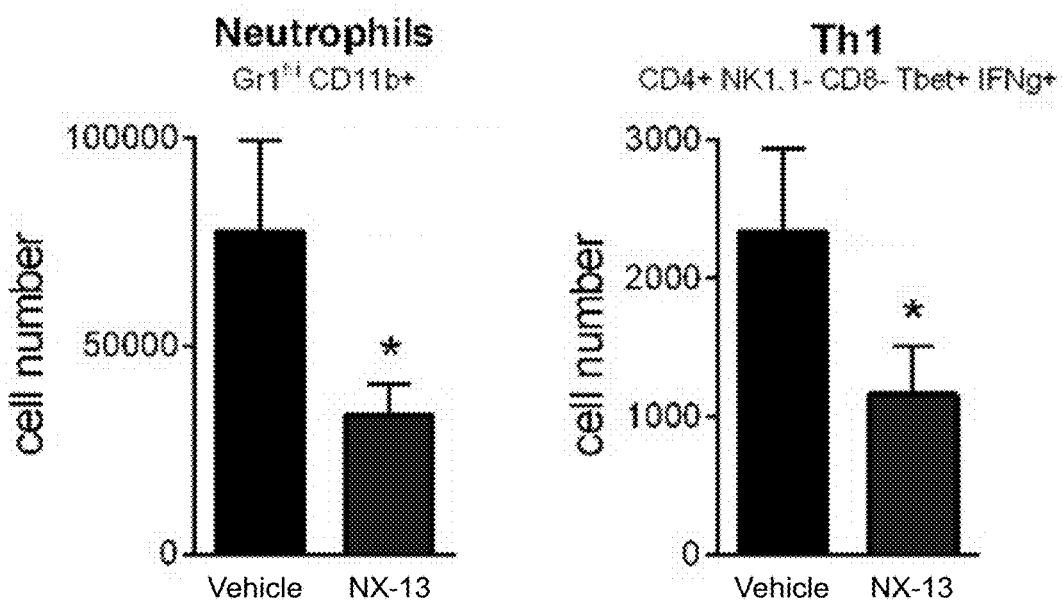
FIG. 7B　　　　FIG. 7C

NLRX1 LIGANDS

FIELD OF THE INVENTION

The present invention relates to ligands of NLRX1 and uses thereof, such as the treatment and prevention of cancers; infectious diseases of bacterial, fungal and viral origin; and inflammatory, immune-mediated, or chronic gastrointestinal diseases such as inflammatory bowel diseases.

BACKGROUND

Nucleotide-binding oligomerization domain, leucine rich repeat containing X1 (NLRX1) (also called "NOD-like receptor X1" or "NLR family member X1" or "NOD9") is a signaling pathway protein that is expressed in immune cells, the gastrointestinal tract, and skin, lung, muscle, endocrine, and reproductive tissues [1]. The NLRX1 molecule has three distinct domains and localizes to the mitochondria [2]. Published results indicate that the loss of NLRX1 worsens disease severity and alters immune cell metabolism [3] in models of inflammatory bowel disease [4-6]. The NLRX1 protein has also been implicated in models of viral responses [7-14], bacterial infection [15], fungal infection [16], cancer [17-21], hepatic steatosis [22, 23], type 2 diabetes [24], brain injury [25], myocardial ischemia [26], chronic obstructive pulmonary disease [27], and autoimmune encephalomyelitis [28].

There are clear unmet clinical needs for safe, efficacious treatments for diseases in which NLRX1 is implicated. These include autoimmune diseases, chronic and inflammatory gastrointestinal diseases, such as inflammatory bowel diseases, cancers, and infectious diseases. Due to low efficacy and poor safety, current autoimmune treatments require frequent monitoring, shifting treatment paradigms, and complex delivery methods. Thus, new treatments capable of being dosed orally for long-term management of disease are needed. In infectious diseases, high mutation rates in various microbes necessitate the development of novel non-antimicrobial treatments that spare the use of antibacterials, antifungals, and antivirals. Further, new strains and epidemic infections create a lag period between the emergence of a pathogen and the availability of microbe-specific interventions, creating a need for novel host-targeted therapeutics. Given the epidemic of infectious and autoimmune diseases as a whole, the NLRX1 pathway has the potential to significantly impact millions of patients.

Viral nucleic acids [29] and dietary lipids have been identified as natural ligands of NLRX1 [5]. There is a need to develop novel ligands of the NLRX1 pathway to allow treatments to be tailored specifically to individual diseases and to potentially maximize their efficacy.

The present invention provides compounds that have been developed by medicinal chemistry approaches and screened using in silico, in vitro, and in vivo techniques, to maximize their ability to bind to the NLRX1 protein and thus to induce a beneficial response in various disease conditions, including but not limited to, cancers, infectious diseases of bacterial, fungal and viral origin, and inflammatory, immune-mediated, or chronic gastrointestinal diseases such as inflammatory bowel diseases.

SUMMARY OF THE INVENTION

The invention provides compounds of formula Z or a pharmaceutically acceptable salt thereof, wherein:
Z is:

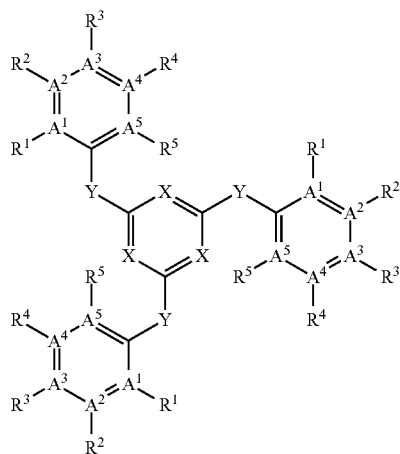

X in each instance is independently selected from the group consisting of N and $CR^6$;

Y in each instance is independently selected from the group consisting of $NR^6$, O, S, $C(R^6)_2$, and $CR^7$;

$A^1, A^2, A^3, A^4$, and $A^5$ in each instance are independently selected from the group consisting of N and C;

$R^1, R^2, R^3, R^4, R^5$, and $R^6$, when present, are in each instance independently selected from the group consisting of hydrogen, hydroxy, acetyl, halo, and carboxyl; a substituted or unsubstituted moiety selected from the group consisting of amino, alkyl, alkoxy, carboxyalkyl, acyl, acylamino aryl, arylalkyl, heteroalkyl, heteroalkoxy, heterocarboxyalkyl, heteroacyl, heteroacylamino, heteroaryl, and heteroarylalkyl; and any combination of the foregoing, with the proviso that any of $R^1, R^2, R^3, R^4$, and/or $R^5$ on a given ring is absent when $A^1, A^2, A^3, A^4$, and/or $A^5$ on the given ring, respectively, is N; and $R^7$ in each instance is independently selected from the group consisting of =O, =S, and =$NR^6$.

In some versions, at least one instance of $A^3$ is C.

In some versions, at least one instance of at least one of $A^1$ and $A^2$ is N.

In some versions, at least one instance of $A^1$ is N. In some versions in which at least one instance of $A^1$ is N, at least one instance of at least one of $R^1, R^2, R^3, R^4$, and $R^5$ is selected from the group consisting of hydroxy, acetyl, halo, and carboxyl; a substituted or unsubstituted moiety selected from the group consisting of amino, alkyl, alkoxy, carboxyalkyl, acyl, acylamino aryl, arylalkyl, heteroalkyl, heteroalkoxy, heterocarboxyalkyl, heteroacyl, heteroacylamino, heteroaryl, and heteroarylalkyl; and any combination of the foregoing. In some versions in which at least one instance of $A^1$ is N, at least one instance of $R^2$ is selected from the group consisting of hydroxy, acetyl, halo, and carboxyl; a substituted or unsubstituted moiety selected from the group consisting of amino, alkyl, alkoxy, carboxyalkyl, acyl, acylamino aryl, arylalkyl, heteroalkyl, heteroalkoxy, heterocarboxyalkyl, heteroacyl, heteroacylamino, heteroaryl, and heteroarylalkyl; and any combination of the foregoing. In some versions in which at least one instance of $A^1$ is N, an instance of $R^2$ on a same ring as the at least one instance of $A^1$ is selected from the group consisting of hydroxy, acetyl, halo, and carboxyl; a substituted or unsubstituted moiety selected from the group consisting of amino, alkyl, alkoxy, carboxyalkyl, acyl, acylamino aryl, arylalkyl, heteroalkyl, heteroalkoxy, heterocarboxyalkyl, heteroacyl, heteroacylamino, heteroaryl, and heteroarylalkyl; and any combination of the foregoing.

In some versions, at least one instance of at least one of $R^1$, $R^2$, $R^3$, $R^4$, and $R^5$ is selected from the group consisting of hydroxy, acetyl, halo, and carboxyl; a substituted or unsubstituted moiety selected from the group consisting of amino, alkyl, alkoxy, carboxyalkyl, acyl, acylamino aryl, arylalkyl, heteroalkyl, heteroalkoxy, heterocarboxyalkyl, heteroacyl, heteroacylamino, heteroaryl, and heteroarylalkyl; and any combination of the foregoing.

In some versions, at least one instance of at least one of $R^1$ and $R^3$ is selected from the group consisting of hydroxy, acetyl, halo, and carboxyl; a substituted or unsubstituted moiety selected from the group consisting of amino, alkyl, alkoxy, carboxyalkyl, acyl, acylamino aryl, arylalkyl, heteroalkyl, heteroalkoxy, heterocarboxyalkyl, heteroacyl, heteroacylamino, heteroaryl, and heteroarylalkyl; and any combination of the foregoing.

In some versions, at least one instance of $R^1$ is selected from the group consisting of hydroxy, acetyl, halo, and carboxyl; a substituted or unsubstituted moiety selected from the group consisting of amino, alkyl, alkoxy, carboxyalkyl, acyl, acylamino aryl, arylalkyl, heteroalkyl, heteroalkoxy, heterocarboxyalkyl, heteroacyl, heteroacylamino, heteroaryl, and heteroarylalkyl; and any combination of the foregoing.

In some versions, $R^1$, $R^2$, $R^3$, $R^4$, and $R^5$, when present, are in each instance independently selected from the group consisting of hydrogen, hydroxy, halo, substituted or unsubstituted amino, and substituted or unsubstituted alkyl.

In some versions, at least one instance of at least one of $R^2$ and $R^4$ is hydrogen or absent.

In some versions, each instance of Y is O.

In some versions, the compound has the structure of:

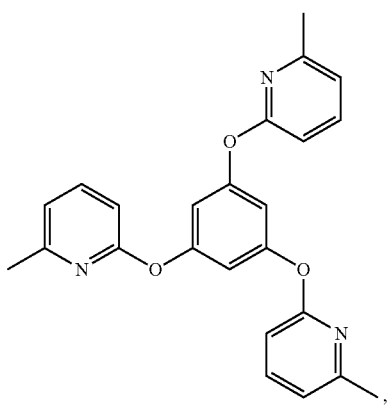

a salt thereof.

In some versions, the compound has the structure of:

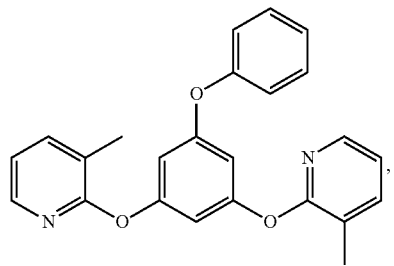 [SMILES: Cc1cccnc1Oc1cc(Oc2ccccc2)cc(Oc2ncccc2C)c1]

or
a salt thereof.

The invention also provides methods of treating a condition in an animal with a compound as described herein. The methods comprise administering an effective amount of the compound to the animal. The condition may be selected from the group consisting of a chronic and/or inflammatory gastrointestinal disease, cancer, and an infectious disease. In some versions, the condition is inflammatory bowel disease. In some versions, the inflammatory bowel disease is ulcerative colitis. In some versions, the inflammatory bowel disease is Crohn's disease. In some versions, the condition is cancer. In some versions, the cancer is colorectal cancer. In some versions, the condition is an infectious disease. In some versions, the infectious disease is a viral disease.

BRIEF DESCRIPTION OF THE DRAWINGS

FIGS. 2A-2D. Computational prediction of binding of selected compounds to NLRX1 in kcal/mol.

FIGS. 7A-7C. In vivo validation of NX-13 efficacy in a DSS model of colitis. Disease activity scores through 7 days of DSS challenge (FIG. 7A) and flow cytometry measures of neutrophil (FIG. 7B) and Th1 (FIG. 7C) populations within the colonic lamina propria on day 7 of mice treated with vehicle or NX-13 daily by oral gavage. Statistical significance ($p<0.05$) is marked by asterisks.

DETAILED DESCRIPTION OF THE INVENTION

General Definitions

Figure 1A:
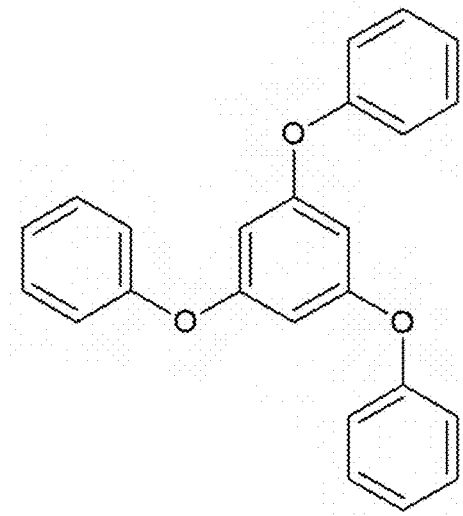
FIGS. 1A-1P. Exemplary compounds of the invention: NX-5 (FIG. 1A), NX-8 (FIG. 1B), NX-9 (FIG. 1C), NX-10 (FIG. 1D), NX-13 (FIG. 1E); NX-35 (FIG. 1F); NX-37 (FIG. 1G); NX-38 (FIG. 1H); NX-41 (FIG. 1I); NX-43 (FIG. 1J); NX-44 (FIG. 1K); NX-45 (FIG. 1L); NX-46 (FIG. 1M); NX-48 (FIG. 1N); NX-49 (FIG. 1O); and NX-50 (FIG. 1P).
Figure 1B:
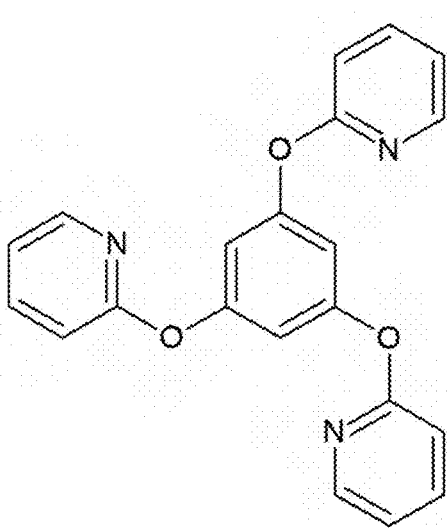
Figure 1C:
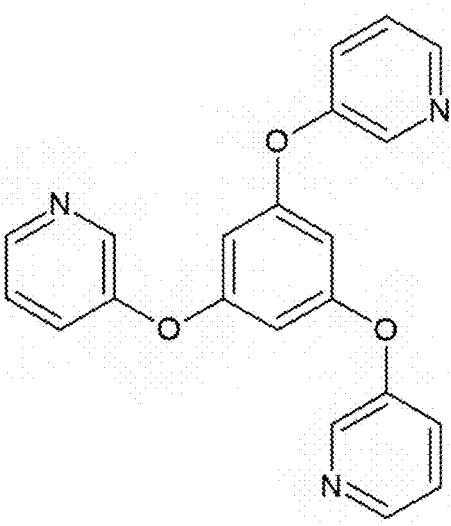
Figure 1D:
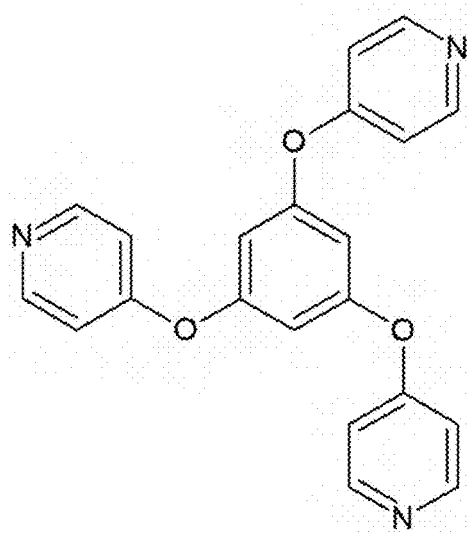
Figure 1E:
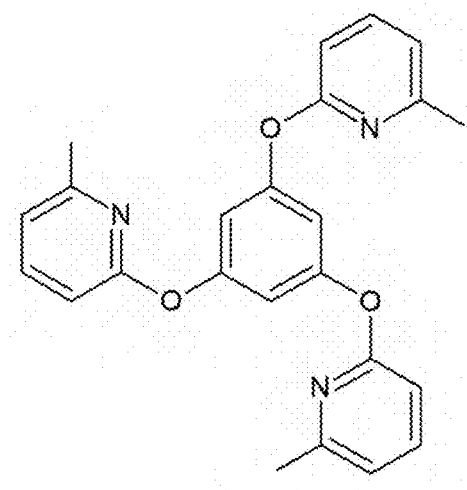
Figure 1F:
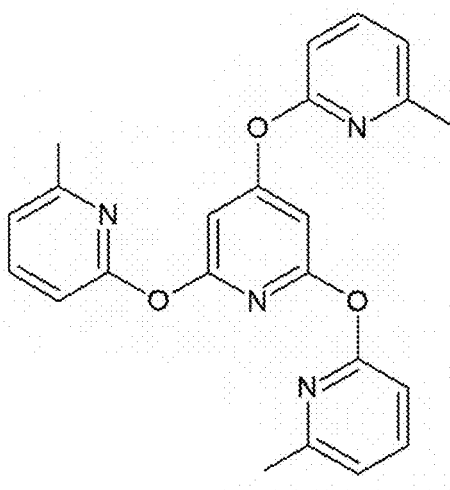
Figure 1G:
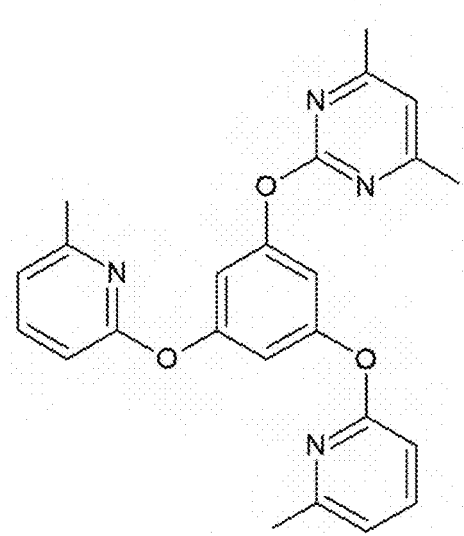
Figure 1H:
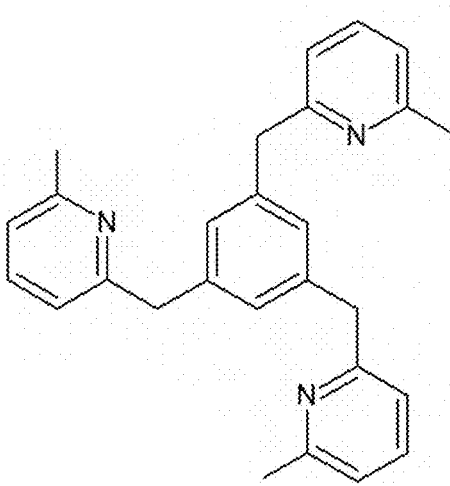
Figure 1I:
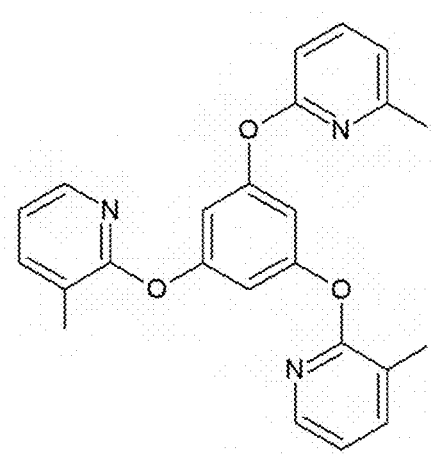
Figure 1J:
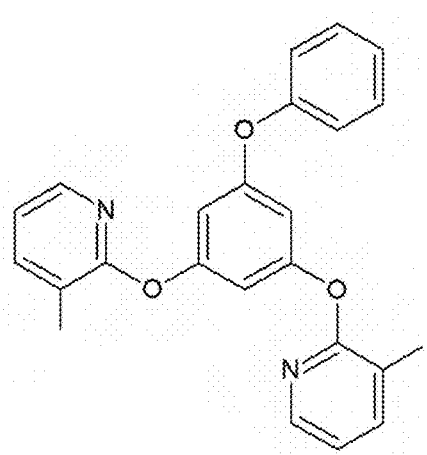
Figure 1K:
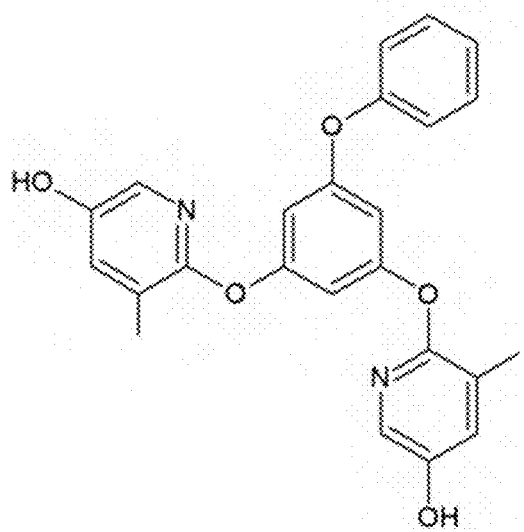
Figure 1L:
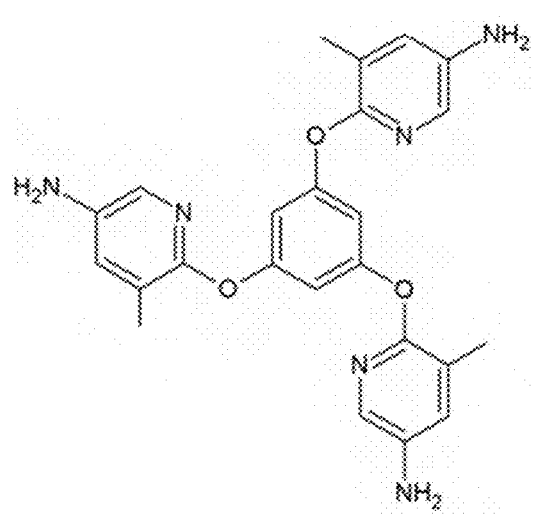
Figure 1M:
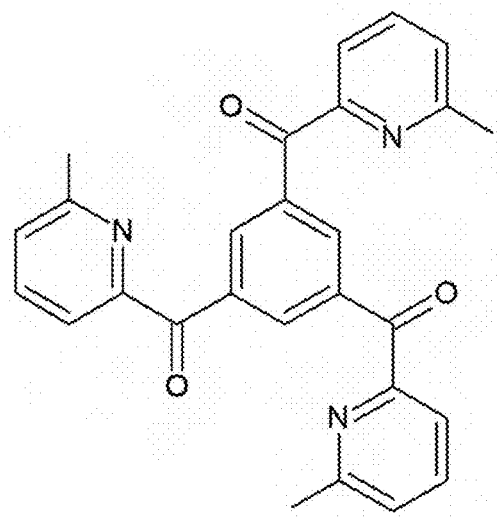
Figure 1N:
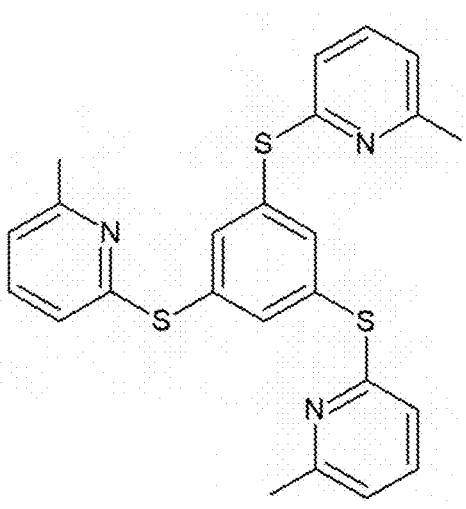
Figure 1O:
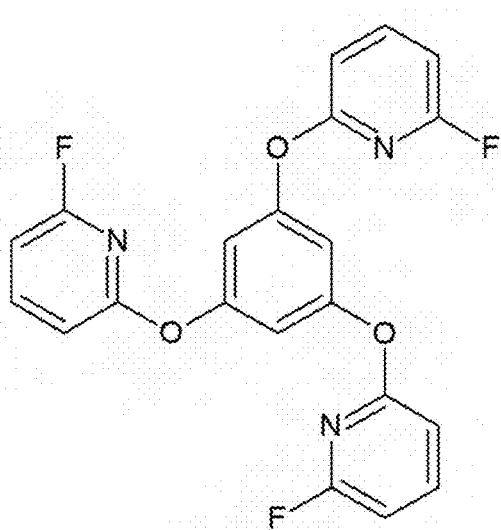

Unless otherwise stated, the following definitions are used throughout the present application:

Analysis of Variance (ANOVA): Arithmetic process for partitioning the overall variation in data sets into specific components based on sources of variation. It has been used to determine whether numerical differences between treatment groups are statistically significant.

Conjugated diene: A molecule containing two double bonds separated by a single bond.

Enantiomer: Optical isomer; chemical classification of molecules based on their ability to rotate the plain of polarization clockwise (+) or anti-clockwise (−).

Substantially pure: Having a purity of at least 90% by weight, preferably at least 95% by weight such as at least 98%, 99% or about 100% by weight.

IBD: Inflammatory bowel disease (IBD) involves chronic inflammation of all or part of the digestive tract. IBD primarily includes ulcerative colitis and Crohn's disease. Both usually involve severe diarrhea, pain, fatigue and weight loss. IBD can be debilitating and sometimes leads to life-threatening complications.

Ulcerative colitis (UC): UC is an IBD that causes long-lasting inflammation and sores (ulcers) in the innermost lining of the large intestine (colon) and rectum.

Crohn's Disease: Crohn's disease is an IBD that cause inflammation of the lining of the digestive tract. In Crohn's disease, inflammation often spreads deep into affected tissues. The inflammation can involve different areas of the digestive tract—the large intestine, small intestine or both.

IL-10: Interleukin-10 (IL-10), also known as human cytokine synthesis inhibitory factor (CSIF), is an anti-inflammatory cytokine. In humans, IL-10 is encoded by the IL10 gene.

FOXP3: FOXP3 (forkhead box P3) also known as scurfin is a protein involved in immune system responses. A member of the FOX protein family, FOXP3 appears to function as a master regulator (transcription factor) in the development and function of regulatory T cells.

TNF-alpha: Tumor necrosis factor (TNF, cachexin, or cachectin, and formerly known as tumor necrosis factor alpha or TNFα) is cytokine involved in systemic inflammation and is a member of a group of cytokines that stimulate the acute phase reaction.

MCP1: Monocyte chemoattractant protein-1. An older term for a CC cytokine which is critical for development of atherosclerotic lesions, found in endothelial cells, macrophages and in vascular smooth muscle cells of patients undergoing coronary artery bypass procedures. The officially preferred term is now chemokine (C—C motif) ligand 2.

Interferon gamma: Interferon gamma is a pro-inflammatory dimerized soluble cytokine that is the only member of the type II class of interferons.

Leukocytic infiltration: Leukocyte infiltration refers to the process of moving or infiltrating of the leukocytes into the injured tissue to begin the repair process.

Chemical Definitions

The term "alkyl," by itself or as part of another substituent, means, unless otherwise stated, a fully saturated, straight, branched chain, or cyclic hydrocarbon radical, or combination thereof, and can include di- and multi-valent radicals, having the number of carbon atoms designated (e.g., $C-C_{10}$ means from one to ten carbon atoms, inclusive). Examples of alkyl groups include, without limitation, methyl, ethyl, n-propyl, isopropyl, n-butyl, t-butyl, isobutyl, sec-butyl, cyclohexyl, (cyclohexyl)ethyl, cyclopropylmethyl, and homologs, and isomers thereof, for example, n-pentyl, n-hexyl, n-heptyl, n-octyl, and the like. The term "alkyl," unless otherwise noted, includes cycloalkyls.

The term "alkenyl" means an alkyl group as defined above except that it contains one or more double bonds. Examples of alkenyl groups include vinyl, 2-propenyl, crotyl, 2-isopentenyl, 2-(butadienyl), 2,4-pentadienyl, 3-(1,4-pentadienyl), etc., and higher homologs and isomers.

The term "alkynyl" means an alkyl or alkenyl group as defined above except that it contains one or more triple bonds. Examples of alkynyl groups include ethynyl, 1- and 3-propynyl, 3-butynyl, and the like, including higher homologs and isomers.

The terms "alkylene," "alkenylene," and "alkynylene," alone or as part of another group means a divalent radical derived from an alkyl, alkenyl, or alkynyl group, respectively, as exemplified by —$CH_2CH_2CH_2CH_2$—.

Typically, alkyl, alkenyl, alkynyl, alkylene, alkenylene, and alkynylene groups will have from 1 to 24 carbon atoms. Those groups having 10 or fewer carbon atoms are preferred in the present invention. The term "lower" when applied to any of these groups, as in "lower alkyl" or "lower alkylene," designates a group having 10 or fewer carbon atoms. Examples of alkyl, alkenyl, alkynyl, alkylene, alkenylene, and alkynylene groups include $C_1$-$C_{10}$, $C_1$-$C_8$, or $C_1$-$C_6$ alkyl, alkenyl, alkynyl, alkylene, alkenylene, or alkynylene groups.

The term "acyl" is a radical of general formula —C(O)R, where R is an alkyl group.

The term "alkoxy" is an alkyl group singularly bonded to oxygen: —O—R, wherein R is an alkyl group. Examples include methoxy, ethoxy, etc.

The term "aryl" is used herein to refer to an aromatic group, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include, for example phenyl, naphthyl, biphenyl, diphenylmethyl and benzophenone, among others. The term "aryl" encompasses "substituted aryl." For phenyl groups, the aryl ring may be mono-, di-, tri-, tetra-, or penta-substituted. Larger rings may be unsubstituted or bear one or more substituents.

The term "arylalkyl" is used herein to refer to a group comprising an aryl and an alkyl group.

The term "carboxyalkyl" is used herein to refer to a group comprising an alkyl and a carboxy group (e.g., —C(O)O($C_1$ to $C_6$) alkyl).

The term "halogen" or "halo" is used herein to refer to fluorine, bromine, chlorine, and iodine atoms.

The term "hetero" appended to the name of any moiety described herein refers to a group in which a non-carbon atom replaces a carbon atom in the moiety. Any moiety described herein can be provided in hetero form. Exemplary heteroatoms include nitrogen, oxygen, sulfur, phosphorus, chlorine, bromine, and iodine, among others.

The term "hydroxy" is used herein to refer to the group —OH.

The term "amino" is used to designate NRR', wherein R and R' are independently H, alkyl, alkenyl, alkynyl, aryl, or substituted analogs thereof. "Amino" encompasses "alkylamino" and "dialkylamino," denoting secondary and tertiary amines. Each alkyl group on the dialkylamino can be independently selected. Amino groups wherein R and R' are H are referred to as "unsubstituted amino" groups. Amino groups wherein R and R' are a moiety other than H are referred to as "substituted amino" groups.

The term "acylamino" is used herein to describe the group RC(O)NR'—, wherein R is an acyl group and R' is independently H, alkyl, alkenyl, alkynyl, aryl, or substituted analogs thereof.

"Substituted" refers to a chemical group as described herein that further includes one or more substituents, such as lower alkyl, aryl, acyl, halogen (e.g., alkylhalo such as $CF_3$), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl, alkenyl, alkynyl, alkylene, alkenylene, alkynylene, or other moieties described herein.

Administration

In the course of the methods of the present invention, a therapeutically effective amount of compounds of the invention can be administered to an animal, including mammals and humans, in many ways. While in the preferred embodiment, the compounds of the invention are administered orally or parenterally, other forms of administration such as through medical compounds or aerosols are also contemplated.

For oral administration, the effective amount of compounds may be administered in, for example, a solid, semi-solid, liquid, or gas state. Specific examples include tablet, capsule, powder, granule, solution, suspension, syrup, and elixir agents. However, the compounds are not limited to these forms.

To formulate the compounds of the invention into tablets, capsules, powders, granules, solutions, or suspensions, the compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, cyclodextrins, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

For parenteral administration, the compounds of the present invention may be administered rectally or by injection. For rectal administration, a suppository may be used. The suppository may be prepared by mixing the compounds of the present invention with a pharmaceutically suitable excipient that melts at body temperature but remains solid at room temperature. Examples include but are not limited to cacao butter, carbon wax, and polyethylene glycol. The resulting composition may be molded into any desired form using methods known to the field.

For administration by injection, the compounds of the present invention may be injected hypodermically, intracutaneously, intravenously, or intramuscularly. Medicinal drugs for such injection may be prepared by dissolving, suspending or emulsifying the compounds of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added. While not required, it is preferred that the composition be sterile or sterilized. To formulate the compounds of the invention into suspensions, syrups, or elixirs, a pharmaceutically suitable solvent may be used. Included among these is the non-limiting example of water.

The compounds of the invention may also be used together with an additional compound having other pharmaceutically suitable activity to prepare a medicinal drug. A drug, either containing a compound of the invention as a stand-alone compound or as part of a composition, may be used in the treatment of subjects in need thereof.

The compounds of the invention may also be administered in the form of an aerosol or inhalant prepared by charging the compounds in the form of a liquid or fine powder, together with a gaseous or liquid spraying agent and, if necessary, a known auxiliary agent such as an inflating agent, into a non-pressurized container such as an aerosol container or a nebulizer. A pressurized gas of, for example, dichlorofluoromethane, propane or nitrogen may be used as the spraying agent.

The compounds of the invention may be administered to an animal, including mammals and humans, in need thereof as a pharmaceutical composition, such as tablets, capsules, solutions, or emulsions. Administration of other forms of the compounds described in this invention, including but not limited to esters thereof, pharmaceutically-suitable salts thereof, metabolites thereof, structurally related compounds thereof, analogs thereof, and combinations thereof, in a single dose or a multiple dose, are also contemplated by the present invention.

The compounds of the invention may also be administered to an animal in need thereof as a nutritional additive, either as a food or nutraceutical supplement.

The terms "preventing," "treating," or "ameliorating" and similar terms used herein, include prophylaxis and full or partial treatment. The terms may also include reducing symptoms, ameliorating symptoms, reducing the severity of symptoms, reducing the incidence of the disease, or any other change in the condition of the patient, which improves the therapeutic outcome.

The compounds described in this invention are preferably used and/or administered in the form of a composition. Suitable compositions are, preferably, a pharmaceutical composition, a foodstuff, or a food supplement. These compositions provide a convenient form in which to deliver the compounds. Compositions of the invention may comprise an antioxidant in an amount effective to increase the stability of the compounds with respect to oxidation or solubility.

The amount of compound that is administered in the method of the invention or that is for administration in the use of the invention is any suitable amount. It is preferably from 1 ng/kg body weight to 20 g/kg body weight, more preferably in the range of 1 μg/kg body weight to 1 g/kg body weight, such as 1 mg/kg body weight to 100 mg/kg body weight of compound per day. Suitable compositions can be formulated accordingly. Those of skill in the art of dosing of biologically active agents will be able to develop particular dosing regimens for various subjects based on known and well understood parameters.

A preferred composition according to the invention is a pharmaceutical composition, such as in the form of tablets, pills, capsules, caplets, multiparticulates (including granules, beads, pellets and micro-encapsulated particles), powders, elixirs, syrups, suspensions, and solutions. Pharmaceutical compositions will typically comprise a pharmaceutically acceptable diluent or carrier. Pharmaceutical compositions are preferably adapted for administration parenterally or orally. Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the compounds on the subject.

Pharmaceutically acceptable carriers suitable for use in such compositions are well known in the art of pharmacy. The compositions of the invention may contain 0.01-99% by weight of the compounds of the invention. The compositions of the invention are generally prepared in unit dosage form. Preferably the unit dosage of compounds described in the present invention is from 0.1 mg to 2000 mg, more preferably from 50 mg to 1000 mg. The excipients used in the preparation of these compositions are the excipients known in the art. Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like. Preferably the unit dosage of compounds described in the present invention is from 0.1 mg to 2000 mg, more preferably from 50 mg to 1000 mg.

In general, the term carrier may be used throughout this application to represent a composition with which the compounds described may be mixed, be it a pharmaceutical carrier, foodstuff, nutritional supplement, or dietary aid. The materials described above may be considered carriers for the purposes of the invention. In certain embodiments of the invention, the carrier has little to no biological activity on the compounds of the invention. Dose: The methods of the present invention can comprise administering a therapeutically effective amount of compound to an animal in need thereof. The effective amount of compound depends on the form of the compound administered, the duration of the administration, the route of administration (e.g., oral or parenteral), the age of the animal, and the condition of the animal, including mammals and humans.

For instance, an amount of a compound effective to treat or prevent ulcerative colitis, Crohn's disease, gastrointestinal inflammation, *Clostridium difficile* infection, colorectal cancer or any other condition described herein in an animal can range from 1 ng/kg/day to 20 g/kg/day. A preferred effective amount of compound is 50 μg/kg/day to 5 g/kg/day, with a more preferred dose being 1 to 100 mg/kg/day. The effective amount of compound is most effective in treating or preventing ulcerative colitis, Crohn's disease, gastrointestinal inflammation, *Clostridium difficile* infection, colorectal cancer of an animal when administered to an animal for periods ranging from about 1 to 1000 days, with a preferred period of 7 to 300 days, and a most preferred period of 30 to 90 days, whereby most effective is defined as an identification of the induction of beneficial responses. The effective amount of compound may be continued beyond these periods for maintenance of beneficial responses in chronic diseases.

An amount of compound most effective in preventing over-activation of the immune system can range from 1 ng/kg/day to 20 g/kg/day, with a preferred dose of 1 to 100 mg/kg/day.

When the effective amount of the compound of the present invention is administered in a nutritional, therapeutic, medical, or veterinary composition, the preferred dose ranges from about 0.01 to 2.0% wt/wt to the food or nutraceutical product.

In certain other embodiments, the present invention provides for use of NLRX1-binding compounds and also structurally related compounds, such as a compound selected from the group consisting the compound, esters thereof, pharmaceutically suitable salts thereof, metabolites thereof, structurally related compounds thereof, or combinations thereof in the treatment and prevention of IBD and gastrointestinal (GI) tract inflammation.

In addition, in general, the present invention relates to inhibition or activation of inflammation in the GI tract, wherein the relevant components include the esophagus, stomach, small intestine, cecum, large intestine, and rectum. The effect results from the exposure of compound to various cells types in the body that induces a biological effect. The cells may include those from GI tract tissues, immune cells (i.e. macrophages, monocytes, lymphocytes), or epithelial cells. In certain embodiments, the invention provides for treating subjects with a compound of the invention, for example as a dietary supplement, to reduce or prevent inflammation related to inflammatory bowel disease, either Crohn's disease or ulcerative colitis. The present invention also contemplates administering the compounds of the invention to the GI tract in order to suppress the expression of cellular adhesion and chemoattractant molecules in the gut.

When practiced, the methods of the invention can be by way of administering the compounds to a subject via any acceptable administration route using any acceptable form, as is described above, and allowing the body of the subject to distribute the compounds to the target cell through natural processes. As is described above, administering can likewise be by direct injection to a site (e.g., organ, tissue) containing a target cell (i.e., a cell to be treated). Furthermore, administering can follow any number of regimens. It thus can comprise a single dose or dosing of experimental compound, or multiple doses or dosings over a period of time. Accordingly, treatment can comprise repeating the administering step one or more times until a desired result is achieved. In certain embodiments, treating can continue for extended periods of time, such as weeks, months, or years. Dosing regimens can preferably entail administration of compound between 6 times daily to once per week, with a more preferred regimen between three times daily to once daily. Those of skill in the art are fully capable of easily developing suitable dosing regimens for individuals based on known parameters in the art. The dosage amounts for compounds of the invention may be used in the methods of these embodiments of the invention. For the treatment of IBD, GI tract inflammation or suppressing expression of cellular adhesion molecules in the gut, it is preferred that the compounds be administered at amounts of about 100 ng/day to 10 g/day.

The amount to be administered will vary depending on the subject, stage of disease or disorder, age of the subject, general health of the subject, and various other parameters known and routinely taken into consideration by those of skill in the medical arts. As a general matter, a sufficient amount of compound will be administered in order to make a detectable change in the amount of inflammation in the GI tract, which with IBD is often related to the amount of pain an individual is experiencing. With patients not currently experiencing IBD symptoms, the change one might look for may involve immune cell parameters such as TNFα or C-reactive protein levels in the blood, the percent of regulatory T-cells in the blood or concentration of calprotectin in feces. Suitable amounts are disclosed herein, and additional suitable amounts can be identified by those of skill in the art without undue or excessive experimentation, based on the amounts disclosed herein.

In one aspect, the invention provides a method of treating or preventing a subject suffering from IBD, or otherwise healthy individuals, perhaps with a genetic predisposition for Crohn's Disease or ulcerative colitis, from developing IBD. The method may also involve treating those with a remissive form of IBD. According to the invention, the term "a subject suffering from IBD" is used to mean a subject (e.g., animal, human) having a disease or disorder showing one or more clinical signs that are typical of IBD. In general, the method of treating or preventing according to this aspect of the invention comprises administering to the subject an amount of compound therapy that is effective in treating or preventing one or more symptoms or clinical manifestations of IBD, or in preventing development of such symptom(s) or manifestation(s).

Thus, according to the methods of the invention, the invention can provide methods of treating IBD, inflammation associated with enteric infection and inflammation associated with autoimmune diseases. The methods of treatment can be prophylactic methods. In certain embodiments, the method is a method of treating IBD, inflammation associated with enteric infection and inflammation associated with autoimmune diseases. In other embodiments, the method is a method of preventing IBD. In embodiments, the method is a method of preventing a remissive form of IBD from becoming active. In still other embodiments, the method is a method of improving the health status of a subject suffering from IBD, inflammation associated with enteric infection and inflammation associated with autoimmune diseases. Organisms causing gastroenteric infections include but are not limited to: *Escherichia coli, Shigella, Salmonella*, pathogenic *Vibrios, Clostridium difficile, Campylobacter jejuni, Yersina enterocolitica, Toxoplasma gondii, Entamoeba histolytica* and *Giardia lamblia*. Accordingly, in certain embodiments, the invention provides a method of protecting the health, organs, and/or tissues of a subject suffering from IBD, inflammation associated with enteric infection and inflammation associated with autoimmune diseases or at risk from developing IBD, inflammation associated with enteric infection and inflammation associated with autoimmune diseases.

In one embodiment of the invention, the method of treating IBD comprises treating IBD without causing discernable side-effects, such as significant weight gain, systemic immune suppression, cushingoid appearance, osteopenia/osteoporosis, or pancreatitis that is common of currently available IBD treatments (i.e. corticosteroids, tumor necrosis factor alpha inhibitors). That is, it has been found that the method of treating according to the present invention, which provides the treatment effect, at least in part, by affecting the expression and/or activation of NLRX1 in some cells, provides the beneficial effect without causing a significant gain in weight, for example by fluid retention, in the subject being treated, as compared to other similar subjects not receiving the treatment.

As such, the methods of the present invention can provide methods of reducing inflammation. The methods can reduce inflammation systemically (i.e., throughout the subject's body) or locally (e.g., at the site of administration or the site of inflammatory cells, including but not limited to T cells and macrophages). In treating or preventing inflammation according to the methods of the present invention, one effect that may be seen is the decrease in the number of blood monocytes or macrophages and lymphocytes infiltrating the intestine. Another may be the increase in regulatory immune cell populations, such as CD4+CD25+FoxP3+ regulatory T-cells, or an increase in regulatory properties of lymphocytes or macrophages (e.g. increased IL-10 or decreased TNF-α and IL-6). Another may be the decreased presence of inflammatory genes and/or adhesion molecules. The methods can thus also be considered methods of affecting or altering the immune response of a subject to whom the compound therapy is administered. The subject may have inflammatory bowel disease or another condition in which the immunomodulation of T cells or downregulation of cellular adhesion molecules is a desired outcome.

The invention provides methods of treating a chronic and/or inflammatory gastrointestinal disease with the compounds described herein. Non-limiting examples of chronic and/or inflammatory gastrointestinal diseases include inflammatory bowel disease (IBD), eosinophilic gastrointestinal disease, Celiac disease, necrotizing enterocolitis, primary sclerosing cholangitis, chronic erosive gastritis, irritable bowel syndrome, small intestinal amyloidosis, ischemic colitis, radiation colitis, diverticulitis, lymphocytic colitis, collagenous colitis, among others.

The methods of the present invention can provide methods of increasing inflammation. The methods can increase inflammation systemically (i.e., throughout the subject's body) or locally (e.g., at the site of administration or the site of inflammatory cells, including but not limited to T cells and macrophages). In treating or preventing inflammation according to the methods of the present invention, one effect that may be seen is the increase in immune cell populations, such as CD4+Tbet+ T helper 1 cells or neutrophils, or an increase in inflammatory cytokine production, such as TNF-α or IFN-γ. The methods can thus also be considered methods of supporting the immune response of a subject to whom the compound therapy is administered. The subject may have an infection or cancer in which the activation of the immune system is beneficial in treating the disease.

The invention also provides methods of treating an infectious disease with the compounds described herein. Non-limiting examples of such infectious diseases include viral infections, bacterial infections, and fungal infections.

Non-limiting examples of viral infections include infections from viruses in the family adenoviridae, such as adenovirus; viruses in the family herpesviridae such as herpes simplex, type 1, herpes simplex, type 2, varicella-zoster virus, epstein-barr virus, human cytomegalovirus, human herpesvirus, and type 8; viruses in the family papillomaviridae such as human papillomavirus; viruses in the family polyomaviridae such as BK virus and JC virus; viruses in the family poxviridae such as smallpox; viruses in the family hepadnaviridae such as hepatitis B virus; viruses in the family parvoviridae such as human bocavirus and parvovirus B19; viruses in the family astroviridae such as human astrovirus; viruses in the family caliciviridae such as norwalk virus; viruses in the family picornaviridae such as coxsackievirus, hepatitis A virus, poliovirus, and rhinovirus; viruses in the family coronaviridae such as acute respiratory syndrome virus; viruses in the family flaviviridae such as hepatitis C virus, yellow fever virus, dengue virus, and West Nile virus, viruses in the family togaviridae such as rubella virus; viruses in the family hepeviridae such as hepatitis E virus; viruses in the family retroviridae such as human immunodeficiency virus (HIV); viruses in the family orthomyxoviridae such as influenza virus; viruses in the family arenaviridae such as guanarito virus, junin virus, lassa virus, machupo virus, and sabia virus; viruses in the family bunyaviridae such as Crimean-Congo hemorrhagic fever virus; viruses in the family filoviridae such as ebola virus and marburg virus; viruses in the family paramyxoviridae such as measles virus, mumps virus, parainfluenza virus, respiratory syncytial virus, human metapneumovirus, hendra virus, and nipah virus; viruses in the family rhabdoviridae such as rabies virus; unassigned viruses such as hepatitis D virus; and viruses in the family reoviridae such as rotavirus, orbivirus, coltivirus, and banna virus, among others.

Non-limiting examples of bacterial infections include infections with the bacteria described above, in addition to *Bacillus anthracia, Bacillus cereus, Bordetella pertussis, Borrelia burgdorferi, Brucella abortus, Brucella canis, Brucella melitensis, Brucella suis Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Tropheryma whippelii* and/or resulting Whipple's disease, *Vibrio cholerae, Yersinia pestis, Yersinia enterocolitica, Yersinia pseudotuberculosis*, and other species from the genera of the above-mentioned organisms.

Non-limiting examples of fungal infections include infection with fungi of the genus *Aspergillus*, such as *Aspergillus fumigatus*, which cause aspergillosis; fungi of the genus *Blastomyces*, such as *Blastomyces dermatitidis*, which cause blastomycosis; fungi of the genus *Candida*, such as *Candida albicans*, which cause candidiasis; fungi of the genus *Coccidioides*, which cause coccidioidomycosis (valley fever); fungi of the genus *Cryptococcus*, such as *Cryptococcus neoformans* and *Cryptococcus gattii*, which cause cryptococcosis; dermatophytes fungi, which cause ringworm; fungi that cause fungal keratitis, such as *Fusarium* species, *Aspergillus* species, and *Candida* species; fungi of the genus *Histoplasma*, such as *Histoplasma capsulatum*, which cause histoplasmosis; fungi of the order Mucorales, which cause mucormycosis; fungi of the genus *Saccharomyces*, such as *Saccharomyces cerevisiae*; fungi of the genus *Pneumocystis*, such as *Pneumocystis jirovecii*, which cause pneumocystis pneumonia; and fungi of the genus *Sporothrix*, such as *Sporothrix schenckii*, which cause sporotrichosis.

The invention also provides methods of treating cancers with the compounds described herein. Non-limiting examples of cancers include colorectal cancer, throat cancer, thyroid cancer, gastric cancer, pancreatic cancer, Hodgkin lymphoma, non-Hodgkin lymphoma, acute myeloid leukemia, hepatocellular cancer, gastrointestinal stromal tumors, acute lymphoblastic leukemia, chronic myeloproliferative disorders, among others.

In view of the above methods, it should be evident that the present invention provides NLRX1-binding compound therapy for use in contacting cells, such as in treating cells of a subject. The above discussion focuses on the use of the compounds of the present invention as part of a composition for use in what could generally be considered a pharmaceutical or medical setting.

The compounds described in this invention for the treatment of IBD, GI tract inflammation, and other conditions described may be formulated as a pharmaceutical, nutritional composition, functional food composition, or dietary aid.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Molecular Modeling

Example 1. Molecular Modeling of NLRX1 Ligands

Using previously described ligands of NLRX1, including viral RNA and dietary lipids (punicic acid and docosahexaenoic acid), we determined the existence of two high-potential binding sites on the NLRX1 protein [5]. These ligands were docked onto the published structure for the C terminus of NLRX1 (pdb: 3UN9) to establish important binding residues.

Methods

Virtual Screening.

To provide additional insights into preliminary scaffolds, ligand databases were docked onto the NLRX1 using AutoDock Vina at each of the two sites using cuboid search grid of size (58×40×40 angstrom) to provide predicted binding affinities and conformations of ligands. Binding affinity was normalized to molecular weight of the ligand. Top ligands were selected for further examination of binding pose.

Compound Generation.

From the identified residues and predicted biochemical interactions, structures were generated for high affinity NLRX1 ligands. Structures were generated and chemically optimized using WebMo. Structure files were generated in .pdb format and converted to .pdbqt format through calculation of charges by Gasteiger method. Structures were docked using AutoDock Vina to confirm binding affinity.

Analysis.

Compounds were preliminarily ranked by lowest predicted binding affinity normalized to molecular weight representing the most favorable binding pose through a minimization of total intermolecular energy, total internal energy and torsional free energy. Compounds were then prioritized based on favorable distances to critical binding residues on NLRX1.

Results

Figure 1P:
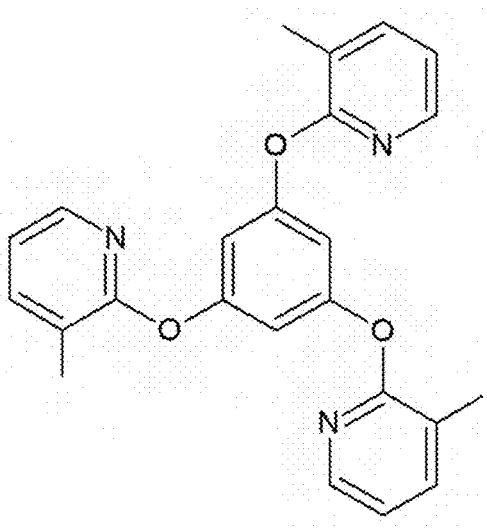
Figure 2A:
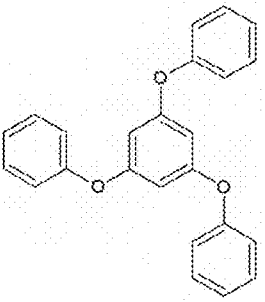
Figure 2A:
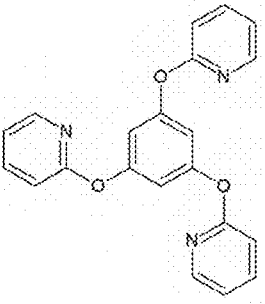
Figure 2A:
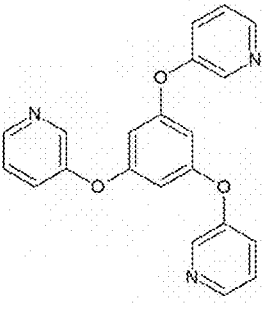
Figure 2A:
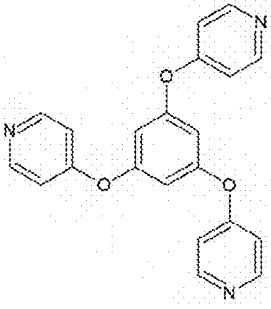
Figure 2D:
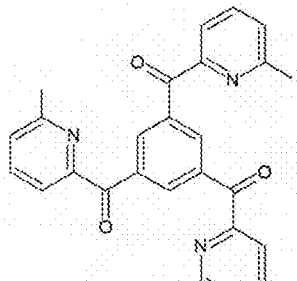
Figure 2D:
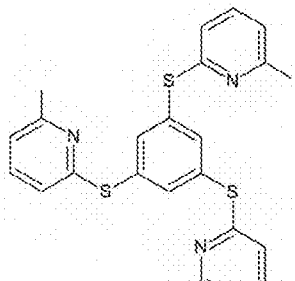
Figure 2D:
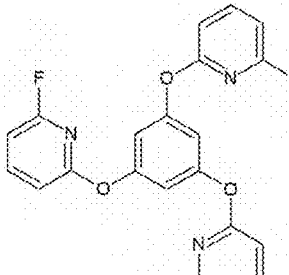
Figure 2D:
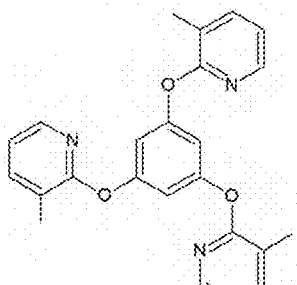

From the virtual screening and optimization of new chemical entities (NCEs), compounds with 120° rotational symmetry and similar pseudosymmetric derivatives of formula Z disclosed herein were identified to have a strong binding affinity to NLRX1. See FIGS. 1A-1P. These NCEs were comprised of compounds with a central benzene or azabenzene ring connected to three outer ring structures by a single linker atom. The binding affinities of selected family members are provided in FIGS. 2A-2D. The predicted binding affinities in the respective lowest energy binding configuration ranged from −8.9 kcal/mol to −11.7 kcal/mol. All the presented compounds have predicted binding affinities higher than that of the low affinity NLRX1 ligand, punicic acid, which has a published binding affinity of −6.2 kcal/mol. A high-affinity-binding compound in this class of NCEs was observed to be 2,2'-(5-phenoxy-1,3-phenylene) bis(oxy)bis(3-methylpyridine), termed NX-43. A high-affinity-binding, fully symmetric compound was observed to be 1, 3, 5-tris (6-methylpyridin-2-yloxy) benzene, termed NX-13, at −10.6 kcal/mol. Replacement of the oxygen linker of NX-13 with a methylene (NX-38), carbonyl (NX-46), or sulfur (NX-48) slightly reduced predicted binding but binding was still above predicted ligand threshold. Based on binding results and predicted physicochemical properties, compounds were selected from this class for synthesis and functional testing.

Medicinal Chemistry

Example 2. NX-13

Potassium Carbonate was added to a solution of benzene-1, 3, 5-triol and 2-bromo-6-methylpyridine in dimethyl formamide and the reaction mixture was irradiated with microwave at 200° C. for 4 h. Reaction mixture was diluted with ice cold water and extracted with ethyl acetate. The combined organic layer was dried with sodium sulfate and evaporated under reduced pressure to obtain of 1, 3, 5-tris (6-methylpyridin-2-yloxy) benzene. HNMR (400 MHz, DMSO-d6): 7.767-7.728 (t, J=8.0 Hz, 3H), 7.042-7.024 (d, J=7.2 Hz, 3H), 6.849-6.829 (d, J=8.0 Hz, 3H), 6.667 (s, 3H), 2.352 (s, 9H).

Example 3. NX-37

The synthesis of 2-(3,5-bis(6-methylpyridin-2-yloxy)phenoxy)-4,6-dimethylpyrimidine (NX-37) was a five-step process as detailed below.

Potassium Carbonate was added to a solution of 5-bromobenzene-1,3-diol and 6-fluoro-2-methylpyridine in dimethyl formamide and the reaction mixture was irradiated with microwave at 200° C. for 4 h. Reaction mixture was diluted with ice cold water and extracted with ethyl acetate. The combined organic layer was dried with sodium sulphate and evaporated under reduced pressure to obtain 6,6'-(5-bromo-1,3-phenylene)bis(oxy)bis(2-methylpyridine).

Cesium Carbonate was added to a solution of 6,6'-(5-bromo-1,3-phenylene)bis(oxy)bis(2-methylpyridine) in ethylene glycol and the reaction mixture was heated at 120° C. for 16 h. Reaction mixture was diluted with water and extracted with ethyl acetate. The combined organic layer was dried with sodium sulphate and evaporated under reduced pressure to obtain 2-(3,5-bis(6-methylpyridin-2-yloxy)phenoxy)ethanol.

Potassium hydroxide was added to a solution of 2-(3,5-bis(6-methylpyridin-2-yloxy)phenoxy)ethanol in dimethylsulfoxide and was heated at 100° C. for 3 h. Reaction mixture was diluted with water and extracted with ethyl acetate. The combined organic layer was dried with sodium sulphate and evaporated under reduced pressure to obtain 3,5-bis(6-methylpyridin-2-yloxy)phenol.

Phosphoric trichloride was added to 4,6-dimethylpyrimidin-2-ol at 0° C. and was heated at 110° C. for 16 h. The solvent was evaporated from the reaction mixture. The reaction was quenched with ice cold water and extracted with ethyl acetate. The combined organic layer was dried with sodium sulphate and evaporated under reduced pressure to obtain 2-chloro-4,6-dimethylpyrimidine.

Potassium Carbonate was added to 3,5-bis(6-methylpyridin-2-yloxy)phenol and 2-chloro-4,6-dimethylpyrimidine in dimethyl formamide and the reaction mixture was irradiated with microwave at 200° C. for 3 h. Reaction mixture was diluted with ice cold water and extracted with ethyl acetate. The combined organic layer was dried with sodium sulphate and evaporated under reduced pressure to obtain 2-(3,5-bis(6-methylpyridin-2-yloxy)phenoxy)-4,6-dimethylpyrimidine. HNMR (400 MHz, CDCl3-$d_6$): 7.56 (t, J=7.6 Hz, 2H), 6.89 (d, J=7.2 Hz, 2H), 6.83 (d, J=2.4 Hz, 2H), 6.78-6.77 (m, 2H), 6.72 (d, J=8.0 Hz, 2H), 2.46 (s, 6H), 2.40 (s, 6H).

Example 4. NX-43

The synthesis of 2,2'-(5-phenoxy-1,3-phenylene)bis(oxy)bis(3-methylpyridine) (NX-43) was a two-step process as detailed below.

Potassium Carbonate was added to a solution of 5-bromobenzene-1,3-diol and 2-fluoro-3-methylpyridine in dimethyl formamide. The reaction mixture was irradiated with microwave at 200° C. for 4 h. Reaction mixture was diluted with ice cold water and extracted with ethyl acetate. The combined organic layer was dried with sodium sulphate and evaporated under reduced pressure to obtain 2,2'-(5-bromo-1,3-phenylene)bis(oxy)bis(3-methylpyridine).

Cesium Carbonate was added to a solution of 2,2'-(5-bromo-1,3-phenylene)bis(oxy)bis(3-methylpyridine), phenol, catalytic copper iodide and dimethyl glycine in DMF and the reaction mixture was irradiated with microwave at 150° C. for 3 h.

Reaction mixture was diluted with ice cold water and extracted with ethyl acetate. The combined organic layer was dried with sodium sulphate and evaporated under reduced pressure to obtain 2,2'-(5-phenoxy-1,3-phenylene)bis(oxy)bis(3-methylpyridine). H NMR (400 MHz, CDCl3-d6): 8.02 (d, J=3.6 Hz, 2H), 7.50 (d, J=7.2 Hz, 2H), 7.35-7.31 (m, 2H), 7.12-7.10 (m, 3H), 6.93-6.90 (m, 2H), 6.61-6.60 (m, 1H), 6.566-6.56 (t, J=2.4 Hz, 2H), 2.29 (S, 6H).

Example 5. NX-44

The synthesis of 6,6'-(5-phenoxy-1,3-phenylene)bis(oxy)bis(5-methyl-3-pyridinol) (NX-44) was a four-step process as detailed below.

Potassium Carbonate was added to a solution of 5-bromobenzene-1,3-diol and 2-fluoro-3-methyl-5-nitropyridine and stirred at room temperature for 16 hours. Reaction mixture was diluted with ice cold water and extracted with ethyl acetate. The combined organic layer was dried with sodium sulphate and evaporated under reduced pressure to obtain 2,2'-(5-bromo-1,3-phenylene)bis(oxy)bis(3-methyl-5-nitropyridine).

Cesium Carbonate was added to a solution of 2,2'-(5-bromo-1,3-phenylene)bis(oxy)bis(3-methyl-5-nitropyridine), phenol, catalytic copper iodide and dimethyl glycine in DMF and the reaction mixture was irradiated with microwave at 150° C. for 3 h. Reaction mixture was diluted with ice cold water and extracted with ethyl acetate. The combined organic layer was dried with sodium sulphate and evaporated under reduced pressure to obtain 2,2'-(5-phenoxy-1,3-phenylene)bis(oxy)bis(3-methyl-5-nitropyridine).

$PtO_2$ was added to a stirred solution of 2,2'-(5-phenoxy-1,3-phenylene)bis(oxy)bis(3-methyl-5-nitropyridine) in methanol. The reaction mixture stirred at room temperature under hydrogen atmosphere for 2 hours. The reaction was monitored by LCMS. The reaction mixture was filtered through celite bed and concentrated the filtrate under reduced pressure to obtain 6,6'-(5-phenoxy-1,3-phenylene)bis(oxy)bis(5-methylpyridin-3-amine).

Sodium nitrite was added to a stirred solution of 6,6'-(5-phenoxy-1,3-phenylene)bis(oxy)bis(5-methylpyridin-3-amine) in aqueous sulfuric acid at 80° C. for 1 h. Reaction mixture was diluted with ice cold water and extracted with ethyl acetate. The combined organic layer was dried with sodium sulphate and evaporated under reduced pressure to obtain 6,6'-(5-phenoxy-1,3-phenylene)bis(oxy)bis(5-methyl-3-pyridinol).

Example 6. NX-45

The synthesis of 6,6',6"-(benzene-1,3,5-triyltris(oxy))tris(5-methylpyridin-3-amine) (NX-45) was a two-step process as detailed below.

Potassium Carbonate was added to a solution of benzene-1, 3, 5-triol and 2-fluoro-3, 6-dimethyl-5-nitropyridine in dimethyl form amide and the reaction mixture was stirred at room temperature for 16 h. Reaction mixture was diluted with ice cold water and extracted with ethyl acetate. The combined organic layer was dried with sodium sulphate and evaporated under reduced pressure to obtain 1,3,5-tris(3-methyl-5-nitropyridin-2-yloxy)benzene.

$PtO_2$ was added to a stirred solution of 1, 3, 5-tris (3-methyl-5-nitropyridin-2-yloxy) benzene in methanol. The reaction mixture stirred at room temperature under hydrogen atmosphere for 2 hours. The reaction was monitored by LCMS. The reaction mixture was filtered through celite bed and concentrated the filtrate under reduced pressure to obtain 6,6',6"-(benzene-1,3,5-triyltris(oxy))tris(5-methylpyridin-3-amine). H NMR (400 MHz, DMSO-d6): 7.390 (d, J=2.4 Hz, 3H), 6.91 (d, J=2.4 Hz, 3H), 6.019 (s, 3H), 5.130 (br s, 6H), 2.051 (s, 9H).

Example 7. NX-50

To a stirred solution of benzene-1,3,5-triol in DMSO was added portionwise to NaH over a period of 2 hours. After that, 2-bromo-3-methyl pyridine was added dropwise and allowed to stir over night at 150° C. Reaction progress was monitored. After the conversion of starting material, reaction mixture was diluted with ice cold water and extracted with ethyl acetate. The combined organic layer was dried over sodium sulphate and evaporated under reduced pressure to obtain 1, 3, 5-tris (3-methylpyridin-2-yloxy) benzene.

Receptor Binding

Example 8. Surface Plasmon Resonance Binding to NLRX1

Introduction

Virtual screening and in silico experimentation are valuable means to identify and prioritize scaffolds of interest when designing new small molecule ligands for a therapeutic target. To validate these findings, numerous in vitro methods exists to determine the affinity of a small molecule to the protein of interest. One particular method is surface plasmon resonance, which is ability to estimate steady state binding by flowing a suspension of ligand over immobilized purified protein. This method was used to evaluate prospective NLRX1 ligands.

Methods

NLRX1 production and purification. Human NLRX1 (www.uniprot.org; UniProtKB—Q86UT6 (NLRX1_HUMAN)) was cloned into *E. coli*, amplified and transfected in *Pichia pastoris*. *P. pastoris* was plated onto adenine selective media. Stable transfected colonies were selected and grown within YPD broth at 30° C. for 24 hours, 240 RPM shaking. Starter culture was used to inoculate base media (1% yeast extract, 2% peptone, 1% sorbitol, 2% yeast nitrogen base) containing biotin and buffered with potassium phosphate. Inoculated base media was incubated for 48 hours at 30° C., 240 RPM. *P. pastoris* was then pelleted by centrifugation and resuspended in expression media (1% sorbitol, 2% yeast nitrogen base) containing biotin and buffered with potassium phosphate. Culture was induced daily for protein production through addition of methanol and incubated for a total of 4 days at 28° C., 240 RPM. After incubation, cells were pelleted by centrifugation and lysed by sonication. Recombinant NLRX1 protein was purified by fast protein liquid chromatography (AktaPrime) using immobilized metal affinity chromatography. Fractions of protein were eluted in 1 mL aliquots and evaluated for NLRX1 content. A mutated NLRX1 protein was generated using similar methods to disrupt binding within the predicted binding site through altering four residues to alanine (D677A, F680A, F681A, and E684A).

Surface Plasmon Resonance.

A Biacore T200 was used to evaluate binding to the NLRX1 protein. NLRX1-WT and NLRX1-Mutant were used as proteins to immobilize onto the CM5 sensor chip. NLRX1-WT was diluted in 10 mM sodium acetate buffer at pH 4.0 and immobilized onto the flow cell to a level of ~3700 RU, using standard amine coupling chemistry. NLRX1-Mutant was diluted in 10 mM sodium acetate buffer at pH 4.0 and immobilized onto the flow cell to a level of ~3100 RU, using standard amine coupling chemistry. 20 mM MOPS, 150 mM NaCl, 5 mM sodium acetate, 1 mM EDTA, 0.05% Tween-20, pH 8.0 buffer (Running buffer) was used as the immobilization running buffer. Based on the immobilized response values, theoretical $R_{max}$ values were calculated. The $R_{max}$ values assume 1:1 interaction mechanism. Overnight kinetics were performed for all analytes binding to the immobilized proteins. The kinetics experiments were performed in the presence of running buffer+1% DMSO. The flow rate of all solutions was maintained at 50 μL/min. Analyte concentrations were 0 μM, 2.5 μM, 5 μM, 10 μM, 20 μM, and 40 μM.

Results

Figure 3:
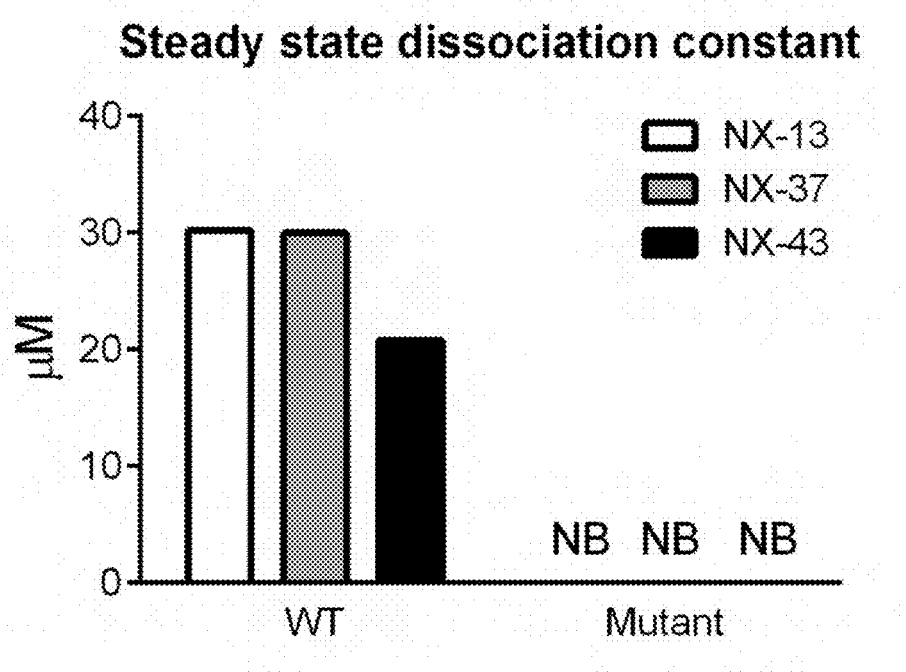
FIG. 3. Experimental validation of NLRX1-binding by selected compounds with surface plasmon resonance (SPR). Presented results are steady state dissociation constants ($K_D$) calculated from 1:1 binding model fitting in micromolar.

Surface plasmon resonance validated the predicted binding of NX-13, NX-37 and NX-43 to NLRX1 (FIG. 3). In particular, NX-13, NX-37 and NX-43 were identified as small molecules that bind to NLRX1 with differing affinities and physicochemical properties. Loss of binding to the mutated NLRX1 protein (FIG. 3) validated that the predicted binding is the main site of binding of these ligands. NX-13 bound to the NLRX1 protein with a $K_D$ of 30.2 μM (FIG. 3).

Experimental Studies

Example 9. Immunological Screening In Vitro

Introduction

Central to the pathogenesis of many autoimmune diseases is the dysfunction of CD4+ T helper cells [3]. These cells are important in maintaining the health of an individual, amplifying immune responses and promoting homeostasis. However, in the case of autoimmune and inflammatory disease, CD4+ T helper cells can become overactive, activated in the absence of stimuli or unable to resolve inflammation. In these scenarios, therapeutics that can mitigate or prevent inflammation are valuable treatments for the management of disease. In this end, we validated the functional therapeutic potential of anti-inflammatory NLRX1 ligands in this cell type.

In contrast to autoimmune diseases, certain infectious diseases and cancer require an increase in inflammatory responses to efficiently control or eliminate the cause of disease [30]. Therefore, therapeutic agents can influence responses in CD4+ T helper cells to enhance immune responses and drive inflammation. In these cases, increases in effector cell types such T helper 1 and T helper 17 cells can benefit the individual through increased production of IFNγ, TNFα, IL-17, and IL-6. As evidenced by published results of NLRX1 in cancer models [17, 18, 21], modulation of the NLRX1 pathway can generate these responses.

Methods

Cell Culture.

Spleens were excised from C57BL/6 mice. Spleens were crushed between the frosted ends of microscope slides and filtered to provide a cellular suspension. Red blood cells were lysed through hypotonic lysis. Remaining cells were washed and filtered. CD4+ T cells were enriched within the suspension using magnetic sorting based negative selection. Cells were collected and plated within 96 well plates coated with anti-CD3 and cultured in the presence of NX-13, NX-37, NX-43, NX-44, or NX-50 at 0, 0.1, 1 or 10 micromolar or NX-45 at 10, 50 or 100 nanomolar for 48 h. During the last 6 h of culture, cells were stimulated with phorbol 12-myristate-13-acetate (PMA) and ionomycin.

Immunological Analysis.

Cells were collected from 96 well plates and stained with a cocktail of antibodies for immunophenotyping by flow cytometry. Culture supernatant was collected and assayed for cytokine concentrations by cytometric bead array. Data was captured on a BD FACS Celesta and analyzed using FacsDiva.

Results

Figure 4A:
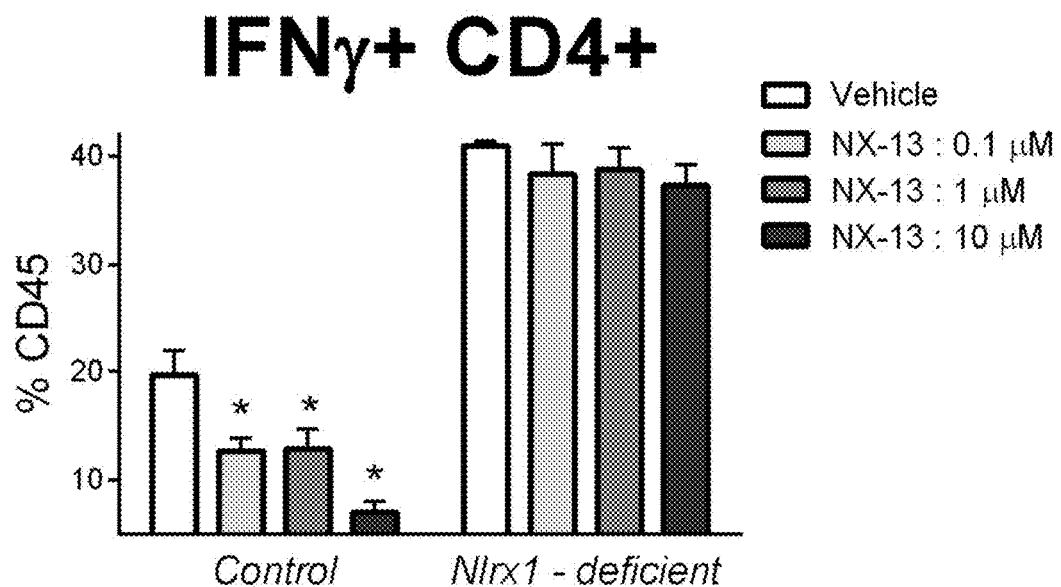
FIGS. 4A and 4B. Immunological validation of NX-13 activity in CD4+ splenocytes. Percentages of IFNγ+ (FIG. 4A) and TNFα+ (FIG. 4B) CD4+ T cells were measured by flow cytometry after in vitro treatment of cells with NX-13 at concentrations of 0.1, 1 and 10 micromolar. Statistical significance (p<0.05) is marked by asterisks.
Figure 4B:
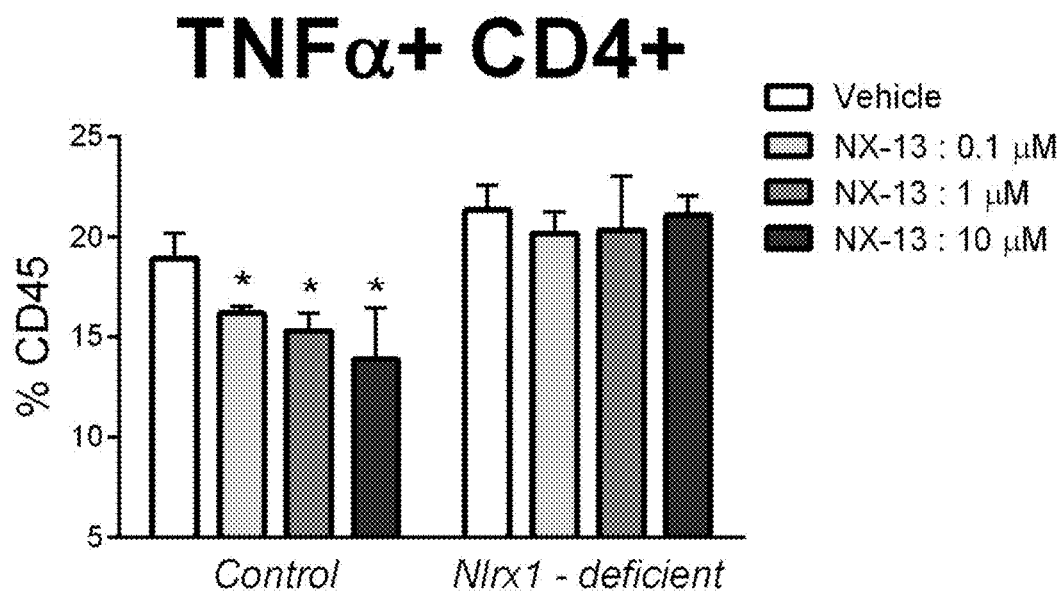

NX-13 reduced proportions of IFNγ producing and TNFα producing CD4+ T cells within wild-type cell culture (FIGS. 4A and 4B). In the absence of NLRX1, these effects were lost (FIGS. 4A and 4B).

Figure 5A:
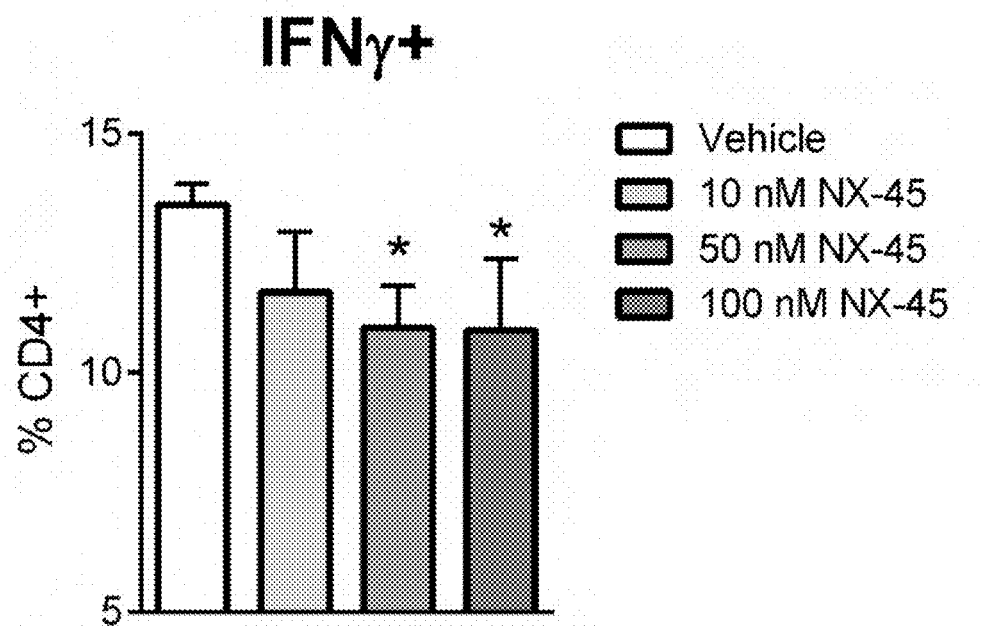
FIGS. 5A-5D. Immunological validation of NX-45 and NX-50 activity in CD4+ splenocytes. Percentages of IFNγ+ (FIGS. 5A and 5C) and TNFα+ (FIGS. 5B and 5D) CD4+ T cells were measured by flow cytometry after in vitro treatment of cells with NX-45 (FIGS. 5A and 5B) or NX-50 (FIGS. 5C and 5D) at concentrations of 10, 50, and 100 nanomolar (NX-45) or 0.1, 1 and 10 micromolar (NX-50). Statistical significance (p<0.05) is marked by asterisks.
Figure 5B:
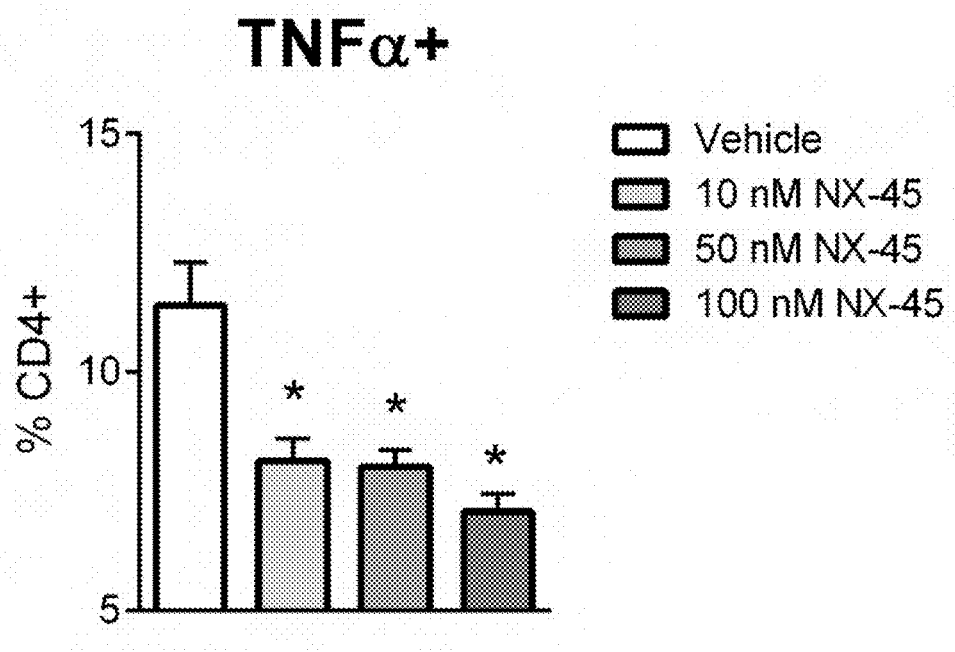
Figure 5C:
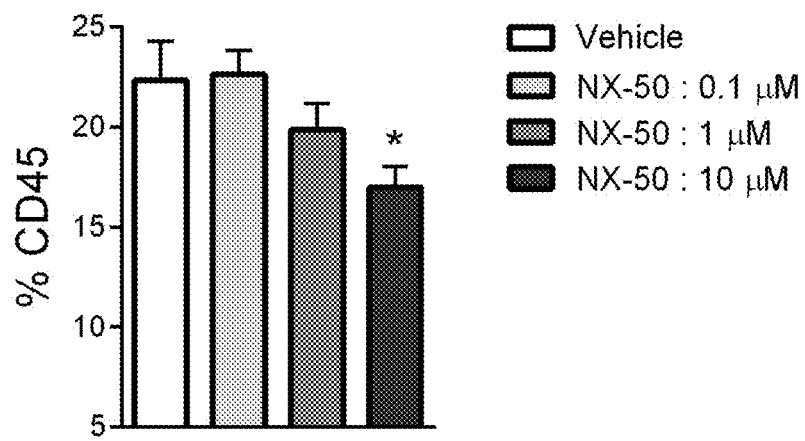
Figure 5D:
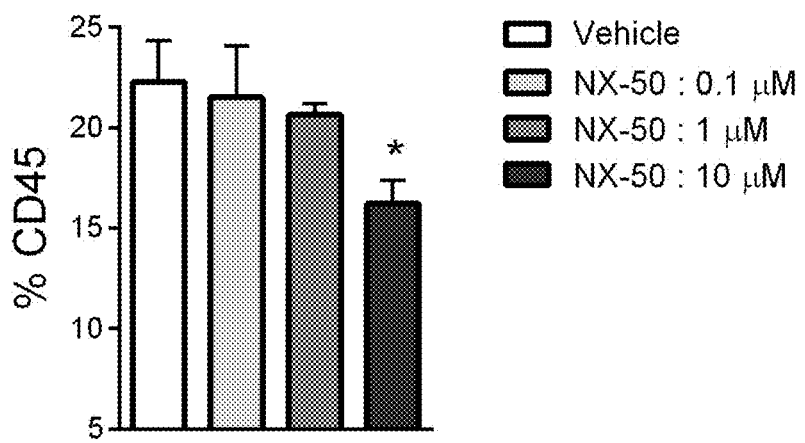
Figure 6A:
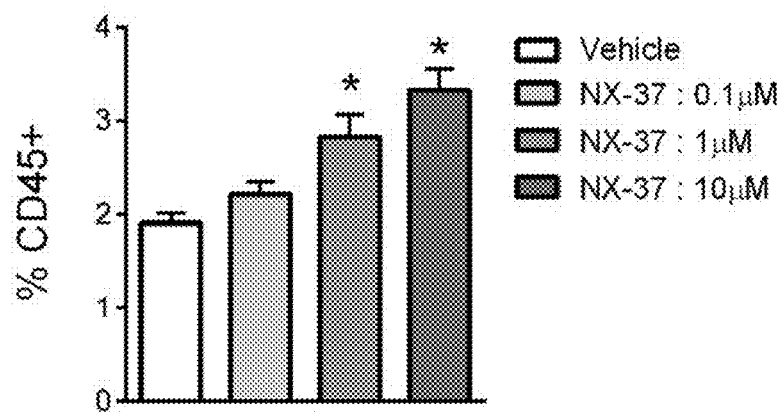
FIGS. 6A-6F. Immunological validation of NX-37, NX-43, and NX-44 activity in CD4+ splenocytes. Percentages of IFNγ+ (FIGS. 6A, 6C, and 6E) and TNFα+ (FIGS. 6B, 6D and 6F) CD4+ T cells were measured by flow cytometry after in vitro treatment of cells with NX-37 (FIGS. 6A and 6B), NX-43 (FIGS. 6C and 6D), or NX-44 (FIGS. 6E and 6F) at concentrations of 0.1, 1 and 10 micromolar. Statistical significance (p<0.05) is marked by asterisks.
Figure 6B:
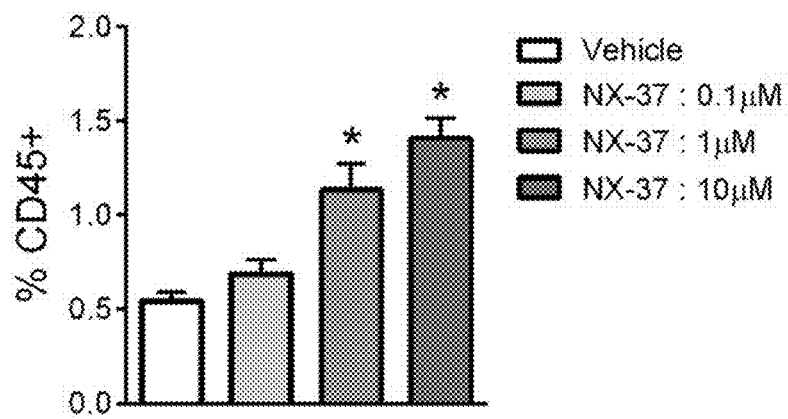
Figure 6C:
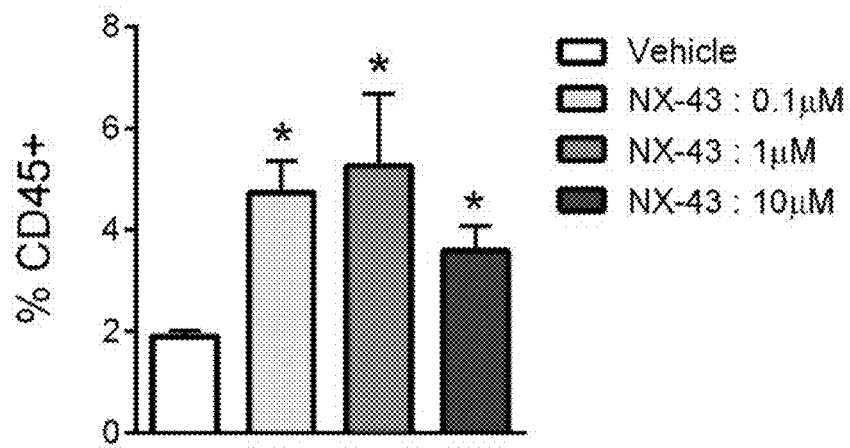
Figure 6D:
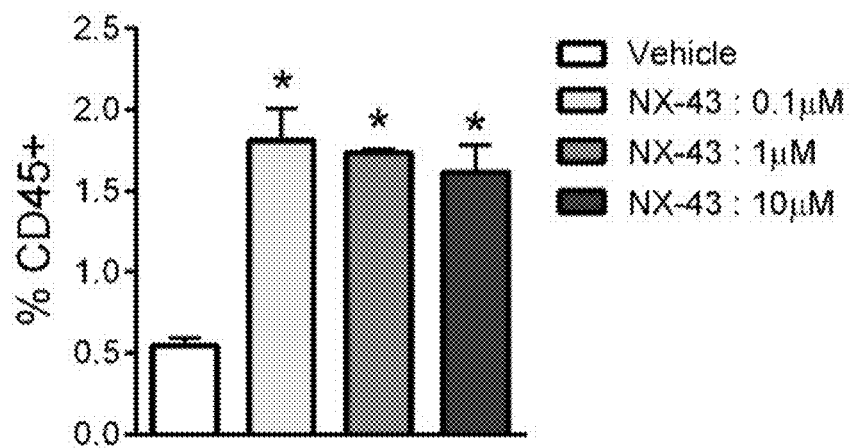
Figure 6E:
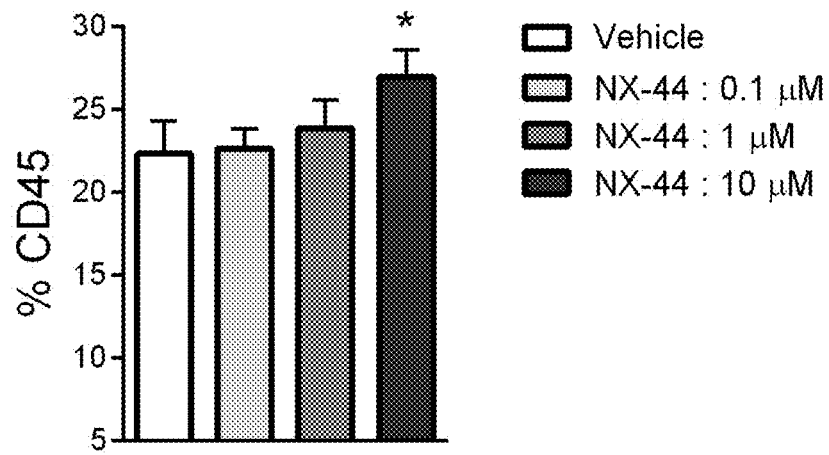
Figure 6F:
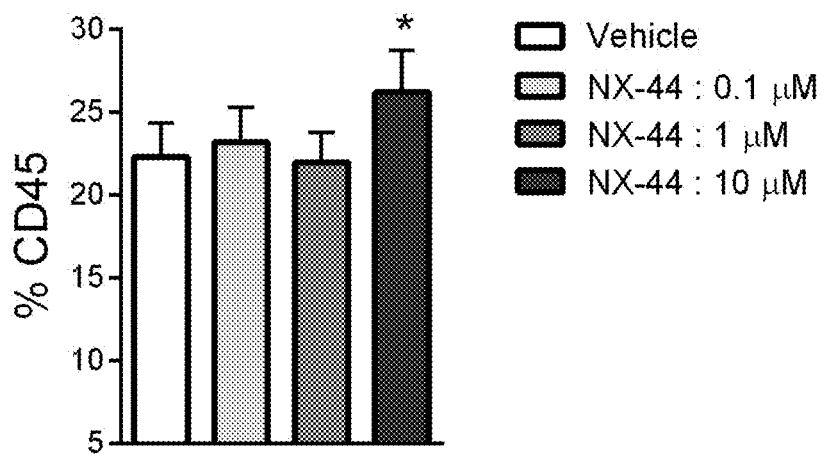

NX-45 was tested at 10, 50 and 100 nanomolar in vitro (FIGS. 5A and 5B). In CD4+ T cells, NX-45 reduces TNFα+ (FIG. 5B) and IFNγ+ (FIG. 5A) cells. The significant reduction in TNFα+ cells occurs at concentrations of 10 nM and higher while the significant reduction in IFNγ+ cells occurs at concentrations of 50 nM and higher. Meanwhile, NX-50 also decreased IFNγ+ and TNFα+ cells albeit at higher concentrations (FIGS. 5C and 5D).

From a downregulation of inflammatory cytokines, these results indicate that NX-13, NX-45 and NX-50 are activators of NLRX1. Given the loss of activity in NLRX1 deficient cells, the family of molecules act through the NLRX1 pathway. Combined with results of in silico and in vitro binding, the actions through the NLRX1 pathway are a result of direct binding to NLRX1.

NX-37, NX-43, NX-44 are both effective in increasing inflammatory responses with distinct signatures (FIGS. 6A-6F). NX-37 (FIGS. 6A and 6B), NX-43 (FIGS. 6C and 6D), NX-44 (FIGS. 6E and 6F) increase the proportion of TNFα (FIGS. 6B, 6D, 6F) and IFNγ (FIG. 6A, 6C, 6E) producing cells as measured by flow cytometry. NX-43 was observed to have a greater effect than NX-37 on TNFα producing cells and IFNγ producing cells, while NX-37 presents with a dose-dependent effects within the range tested. Neither small molecule elicited a change in IL-10 producing cells.

Based on the described results and published knowledge on the NLRX1 pathway, NX-37, NX-43, and NX-44 function as specific inhibitors of NLRX1 through direct binding. The observed increase in inflammatory responses with treatment of these inhibitors is in line with the observation that a deficiency in NLRX1 results in greater inflammation.

Example 10. Use of NX-13 in an Acute Model of IBD

Introduction

Inflammatory bowel disease is a multifactorial disease with many disease processes initiated by actions or dysfunction of the epithelial barrier [31]. A prominent and accepted animal model of the disease is induced by the administration of dextran sulfate sodium (DSS) in the drinking water of mice. Intake of DSS acts to disrupt and destroy the epithelial barrier in the distal gastrointestinal tract, in particular the colon. The disruption of the epithelial barrier allows for infiltration of the microbiome in the colonic mucosa and the ensuing recruitment and activation of immune cells. This model allows for assessment of new therapeutics in a controlled system of intestinal inflammation.

Previously, the DSS model has been used to determine that mice deficient in NLRX1 had worsened disease severity compared to wild-type mice that express NLRX1 [3, 4]. Additionally, when the expression of NLRX1 in wild-type mice was assessed throughout the DSS time course, NLRX1 was suppressed in periods of high inflammation suggesting that the pharmacological activation of the molecule could protect against this decreased expression and induce beneficial anti-inflammatory actions.

Methods

DSS Model.

Mice were given 8% (w/v) DSS in drinking water for seven days to induce disruption of the epithelial layer. At project initiation, mice were 8 weeks of age and began dosing 24 hours after being placed on 8% DSS. Mice were weighed and scored daily for symptoms of disease (diarrhea, rectal bleeding, rectal inflammation, overall behavior). Treatment administration. NX-13 was prepared within a 0.5% methylcellulose (12-15 cP) solution. Dosage used was 20 mg/kg delivered once daily. Mice were weighed on a weekly basis to update dosage formulation. Dosage was calculated based off mean body weights for each gender. Oral dosage was delivered by orogastric gavage of dosage in 0.2 mL volume.

Flow Cytometry.

Colons were collected into RPMI/FBS buffer containing collagenase (300 U/mL) and DNase (50 U/mL) for digestion. Tissues were digested for 60 minutes under stirring at 37° C. Resultant cellular suspensions were filtered through 100 μm strainers, centrifuged (300×g, 8 min), and washed in fresh RPMI. Following filtration of the resulting single cell suspensions, immune cells were purified by Percoll gradient of cell-containing 40% Percoll overlayed onto 70% Percoll solution. After centrifugation, interphase was collected and washed to obtain enriched colonic lamina propria cell fractions. Cells were labeled with mixtures of extracellular (CD45, CD3, CD4, CD8, CD19, NK1.1, CD25, F4/80, CD11b, Gr1, CX3CR1, CD64) and intracellular (Tbet, RORγT, FOXP3, IFNγ, IL17, IL10) antibodies in a sequential live staining in 96-well plates. Data was acquired using a FACS Celesta flow cytometer with FACSDiva software.

Gene Expression.

Total RNA from colon and cells was generated using the Qiagen RNeasy mini kit. cDNA was generated using the BioRad iScript cDNA synthesis kit. Standard curves were generated by serial dilution of purified product from a standard PCR reaction with Taq DNA polymerase followed by purification using the Qiagen MinElute PCR purification kit. Expression levels were obtained from quantitative real-time PCR with SybrGreen supermix on a BioRad CFX96 Thermal cycler followed by normalization to expression of β-actin.

Results

Oral NX-13 treatment decreases the disease activity of wild-type mice challenged with DSS. Disease activity in this model of colitis is a summarized score of the weight loss, presence and severity of rectal bleeding, fecal consistency, symptoms of pain and overall behavior of a mouse. NX-13 reduced disease activity throughout the course of the challenge with a maximal observed reduction by 50% on day 6 (FIG. 7A).

Within the DSS model, disease is initiated at the epithelium but modulated by the presence and abundance of immune cells within the colonic lamina propria. Primary drivers of inflammation and tissue damage in this model are T helper 1 cells and neutrophils. Oral NX-13 treatment significantly reduced the number of Th1 and neutrophil cells in the colonic lamina propria as measured by flow cytometry. On day 7 of DSS challenge, both neutrophils (FIG. 7B) and Th1 cells (FIG. 7C) were reduced by more than 50%. However, NX-13 did not reduce the number of FOXP3+ regulatory CD4+ T cells, which are a primary cell type in the colon responsible for tissue homeostasis.

Figure 8A:
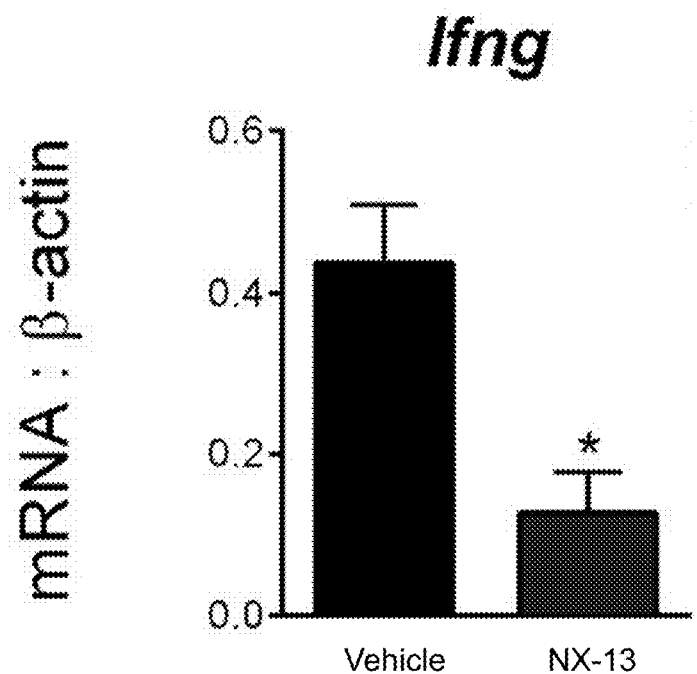
FIGS. 8A-8D. Colonic gene expression following NX-13 treatment. Measurement of Ifng (FIG. 8A), Il10 (FIG. 8B), Tnf (FIG. 8C), and Il17 (FIG. 8D) by quantitative real-time PCR from whole colon RNA of mice challenged with DSS for 7 days and treated with vehicle or NX-13 daily by oral gavage. Data is normalized to beta-actin. Statistical significance ($p<0.05$) is marked by asterisks.
Figure 8B:
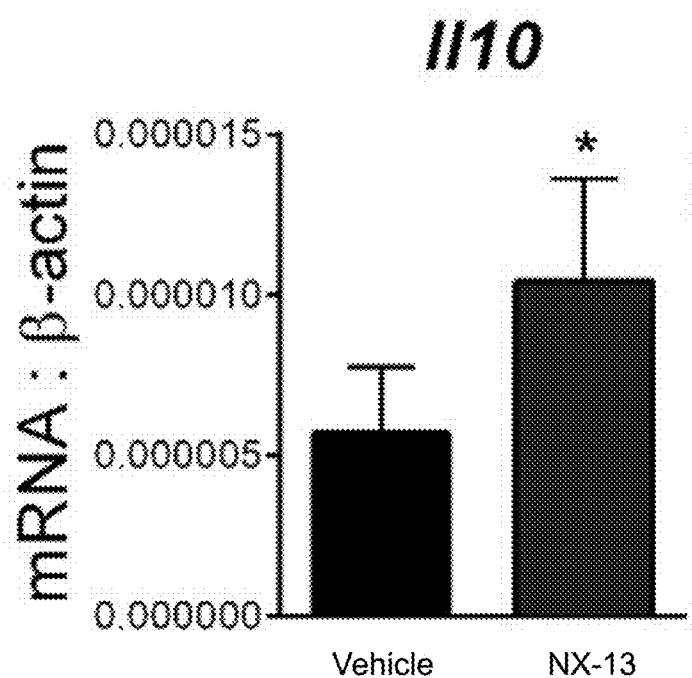
Figure 8C:
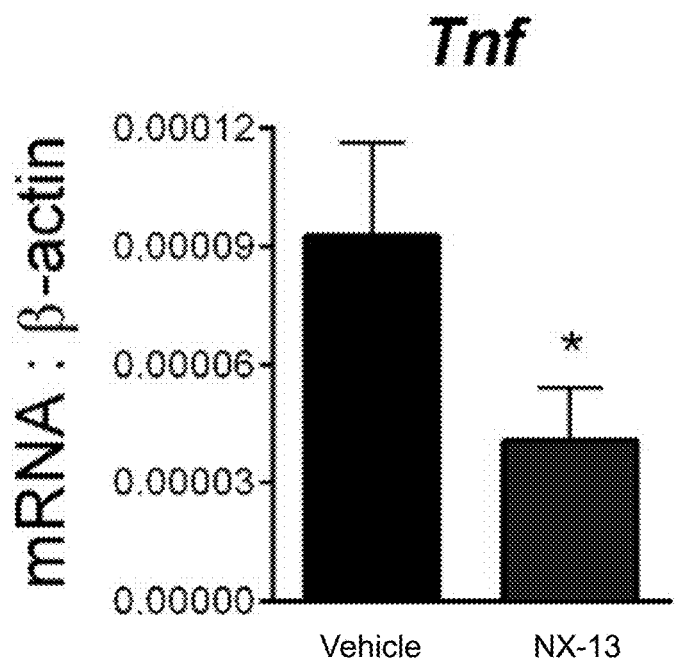
Figure 8D:
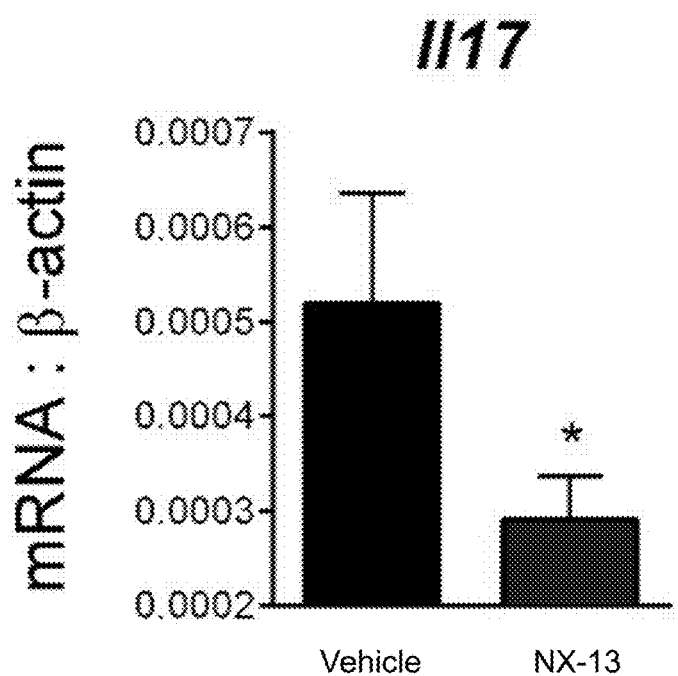

RNA was isolated from the whole colon of vehicle and NX-13 treated mice at day 7 of DSS challenge. RNA was used to measure gene expression of inflammatory and anti-inflammatory cytokines (FIGS. 8A-D). NX-13 treatment reduced expression of Ifng (FIG. 8A), Tnfa (FIG. 8C), and Il17 (FIG. 8D) in the whole colon, while increasing expression of Il10 (FIG. 8B). Importantly, IFNγ and TNFα are two primary drivers of inflammation in IBD. The reduction of these cytokines at the colonic level after oral treatment with NX-13 is a key marker of efficacy.

Example 11. Use of NX-13 in a Chronic Model of IBD

Introduction

Crohn's disease and ulcerative colitis are chronic diseases with sporadic periods of unresolved inflammatory flares resulting in progressive damage to the intestinal mucosa [32, 33]. The loss of Mdr1a in mice impairs the ability of epithelial cells to correctly process and efflux waste products leading to spontaneous colitis [34]. The colitis in these mice is chronic and penetrates throughout the layers of the intestine. The Mdr1a−/− model is therefore an ideal model to test the chronic administration of a therapeutic for the induction and maintenance of decreased disease severity [35] due to its use of immunocompetent animals, the intrinsic dysfunction of epithelial cell mechanisms, prominent inflammatory responses and the translational relevance of the MDR1 gene as an emerging risk allele in human IBD [36].

Methods

MDR1a−/− model. Mice deficient in MDR1a spontaneously develop colitis. MDR1a−/− began receiving NX-13 treatment (oral, 20 mg/kg) at 4 weeks of age and continued treatment until 10 weeks of age. Mice were weighed and scored weekly.

Treatment Administration.

NX-13 was prepared within a 0.5% methylcellulose (12-15 cP) solution. Dosage used was 20 mg/kg delivered once daily. Mice were weighed on a weekly basis to update dosage formulation. Dosage was calculated based off mean body weights for each gender. Oral dosage was delivered by orogastric gavage of dosage in 0.2 mL volume.

Flow Cytometry.

Colons were collected into RPMI/FBS buffer containing collagenase (300 U/mL) and DNase (50 U/mL) for digestion. Tissues were digested for 60 minutes under stirring at 37° C. Resultant cellular suspensions were filtered through 100 μm strainers, centrifuged (300×g, 8 min), and washed in fresh RPMI. Following filtration of the resulting single cell suspensions, immune cells were purified by Percoll gradient of cell-containing 40% Percoll overlayed onto 70% Percoll solution. After centrifugation, interphase was collected and washed to obtain enriched colonic lamina propria cell fractions. Cells were labeled with mixtures of extracellular (CD45, CD3, CD4, CD8, CD19, NK1.1, CD25, F4/80, CD11b, Gr1, CX3CR1, CD64) and intracellular (Tbet, RORγT, FOXP3, IFNγ, IL17, IL10) antibodies in a sequential live staining in 96-well plates. Data was acquired using a FACS Celesta flow cytometer with FACSDiva software.

Histopathology.

H&E stained colonic sections were prepared from portions of colons collected into 10% buffered formalin and embedded in paraffin. Slides were examined by a board-certified veterinary pathologist via an Olympus microscope and images were collected with Image-Pro software. Samples were scored (0-4) for leukocytic infiltration, epithelial erosion and mucosal thickening.

Results

Figure 9:
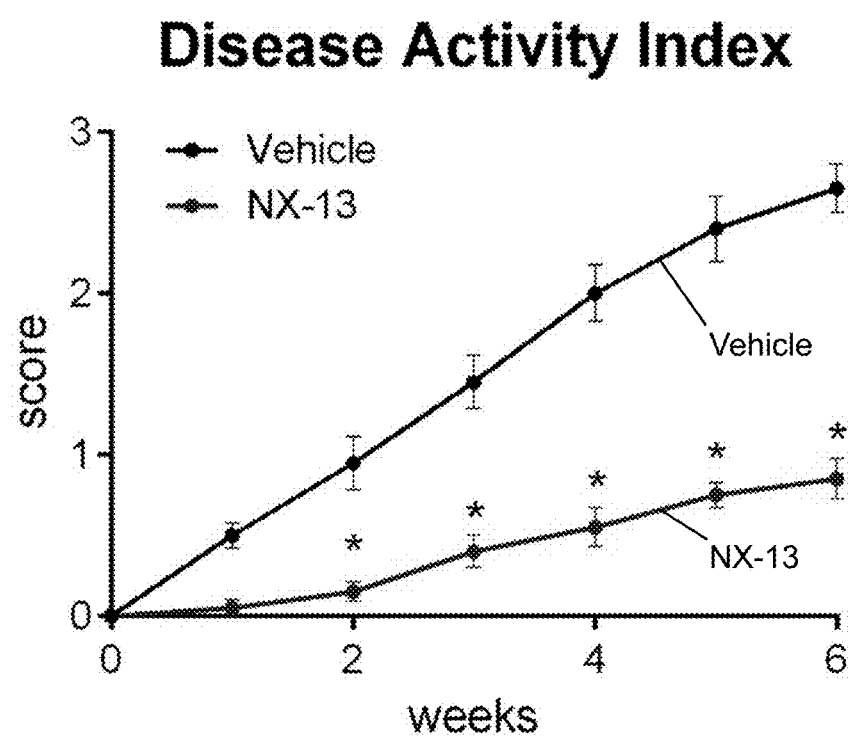
FIG. 9. In vivo validation of NX-13 efficacy in an MDR1a-/- model of colitis. Disease activity scores weekly over the course of the six-week treatment period in which MDR1a-/- were treated with vehicle or NX-13 daily by oral gavage. Statistical significance ($p<0.05$) is marked by asterisks.

Oral NX-13 treatment decreases the disease activity of Mdr1a−/− mice. Disease activity in this model of colitis is a summarized score of the weight loss, presence and severity of rectal bleeding, fecal consistency, symptoms of pain and overall behavior of a mouse. NX-13 reduced disease activity throughout the course of the challenge with a maximal observed reduction by 70% in week six of treatment (FIG. 9).

Figure 10A:
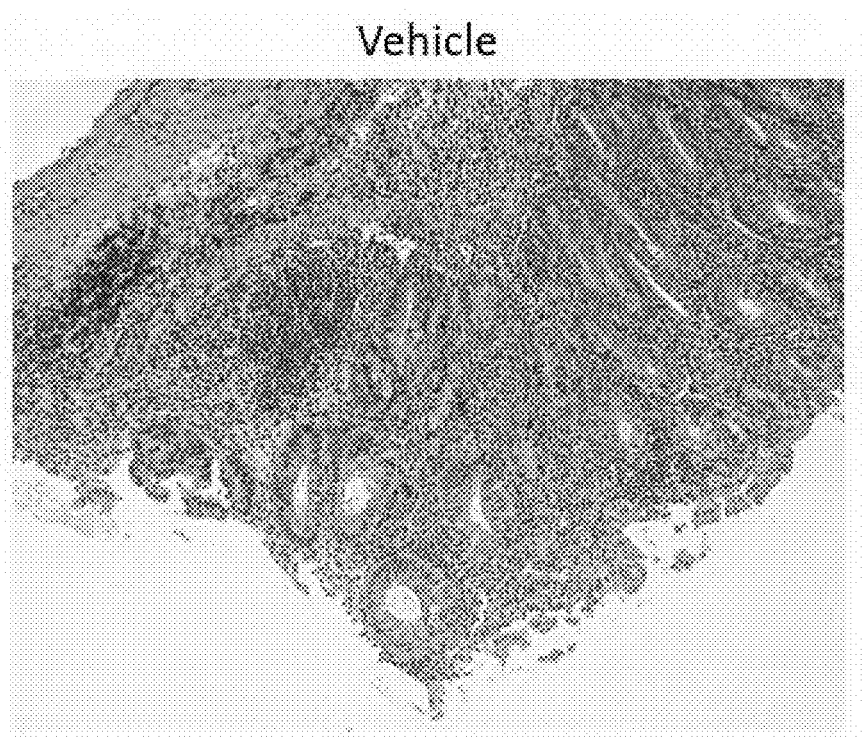
FIGS. 10A and 10B. Representative photomicrographs of H&E stained colonic sections from MDR1a-/- mice after six weeks of treatment with vehicle (FIG. 10A) or NX-13 (FIG. 10B).
Figure 10B:
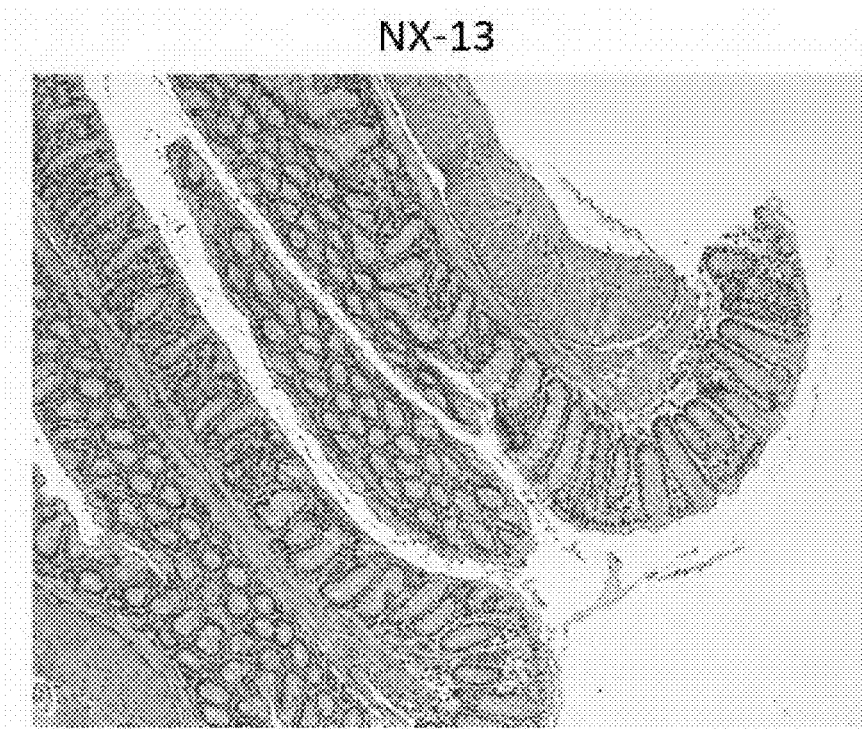

In MDR1a−/− mice, oral NX-13 greatly reduced colonic pathology (FIGS. 10A and 10B). After six weeks of treatment, NX-13 protected against the development of leukocyte aggregates and thickening of the mucosa. Further, NX-13 reduced overall leukocytic infiltration and epithelial erosion.

Figures 11A, 11B, 11C:
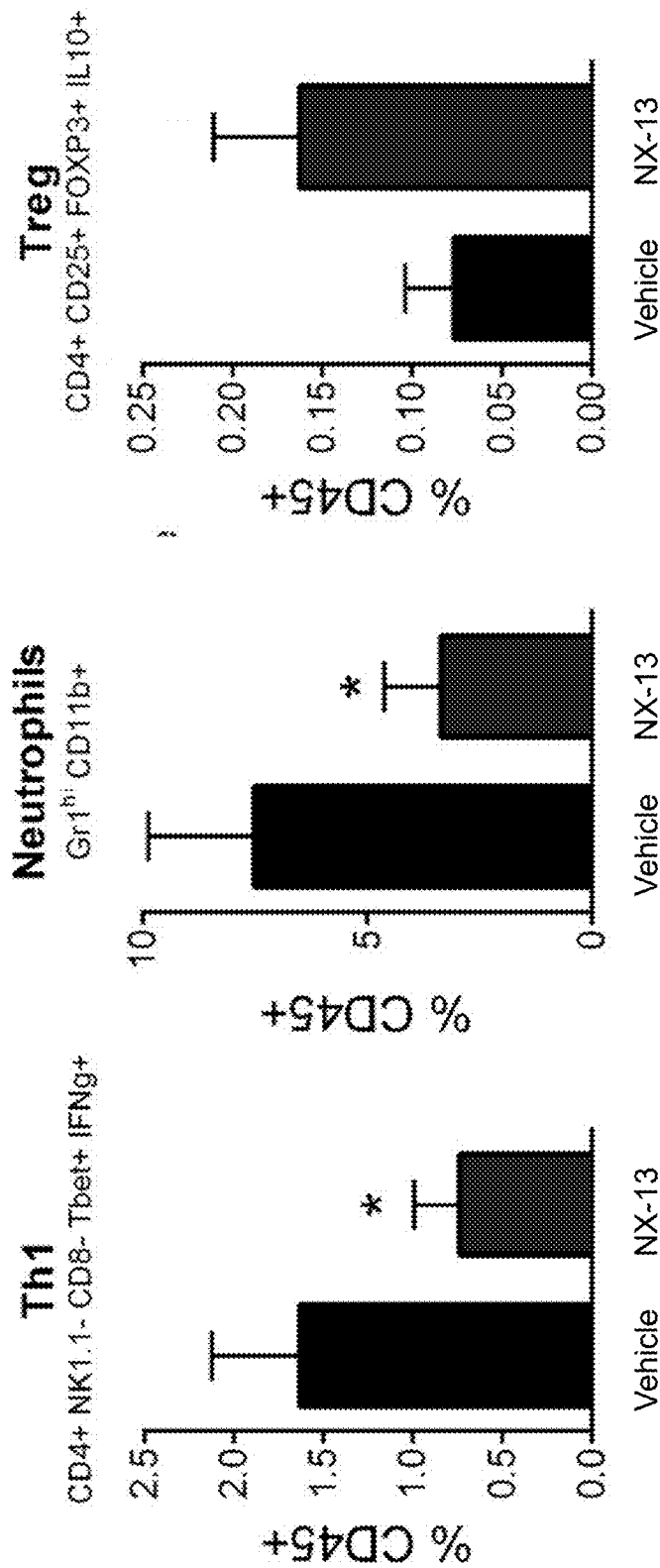
FIGS. 11A-11C. Flow cytometry of the colonic lamina propria of MDR1a-/- mice after six weeks of treatment with vehicle or NX-13 to detect Th1 (FIG. 11A), neutrophil (FIG. 11B), and Treg (FIG. 11C) cellular populations. Statistical significance ($p<0.05$) is marked by asterisks.

Oral NX-13 significantly alters the proportions of immune cells within the colonic lamina propria (FIGS. 11A and 10B). In particular, NX-13 reduces the proportions of Th1 (FIG. 11A) and neutrophils (FIG. 11B), two main subsets of cells responsible for the inflammation in the colonic mucosa. Further, numbers of F4/80hi macrophages as well as IL-17 and IFNγ producing T cells were greatly reduced with NX-13 treatment. Proportions of regulatory CD4+ T (Treg) cells (FIG. 11C) were also increased in the colon. These findings indicate that NX-13 is able to restore the balance between inflammatory and anti-inflammatory responses in the colons of colitic mice.

Example 12. Efficacy of NX-13 in Human Peripheral Blood Mononuclear Cells

Introduction

Humans afflicted with Crohn's disease and ulcerative colitis present with overactive immune cells with high prevalence of inflammatory subsets locally within the gastrointestinal tract and systemically within blood. Therefore, mononuclear cells isolated from peripheral blood (PBMCs) of IBD patients often exhibit many of the robust inflammatory responses observed in the GI mucosa due to the environment to which they are exposed and the genetic abnormalities that are present within all cells of the individual. The translational application of NX-13 was tested in PBMCs from ulcerative colitis and Crohn's disease patients to determine the anti-inflammatory benefit of NX-13 treatment in human cells.

Methods

PBMC Isolation.

Samples were obtained from male and female donors clinically categorized as having moderate to severe disease. Age and current medications were not used as exclusion criteria. Whole blood was collected into heparinized vacuum tubes. Whole blood was diluted 1:3 volumes with sterile phosphate buffered saline. LeucoSep (Greiner) were prepared by addition of Lymphocyte Separation Media followed by 15 second centrifugation at max speed. Diluted whole blood was added to LeucoSep tubes. After centrifugation (2000×g, 20 min), PBMCs were collected from the interphase by Pasteur pipette. Remaining red blood cells were lysed by hypotonic lysis and suspension was filtered through a 100 μM cell strainer. PBMCs were washed and re-suspended in sterile cell culture media, RPMI containing 10% fetal bovine serum, 2.5% Hepes solution, 1% L-glutamine, 1% penicillin/streptomycin, 1% sodium pyruvate, and 1% essential amino acids (complete RPMI).

Cell Culture.

Target cells were incubated for 24 h in complete RPMI culture media at 37° C. Cells were incubated in the presence of NX-13 ranging in concentration from 1 nM to 100 nM. NX-13 stock solution was prepared at 100 mM in dimethyl sulfoxide (DMSO) and diluted to desired concentration in culture media. DMSO concentrations were adjusted to be equal across all doses and vehicle treatments. Six hours prior to assay, cells were stimulated with phorbol 12-myristate 13-acetate (PMA) and ionomycin to stimulate cellular activation. Cells were assayed for desired data at 24 h.

Flow Cytometry.

Prior to collection, cells were incubated BD GolgiStop (2 μL GolgiStop to 3 mL of total media) to allow intracellular accumulation of cytokines. Cells were live stained with extracellular (CD45, CD3, CD4, CD8, CD11b) and intracellular (FOXP3, IL-10, IL-4, IFNγ, TNFα) in a sequential manner. Data was acquired on a BD FACs Celesta and analyzed using FACSDiva. Non-viable and non-singlet cells were excluded from analysis. Data is presented as percentage of CD45+ cells or % viable, singlets.

Results

Figure 12A:
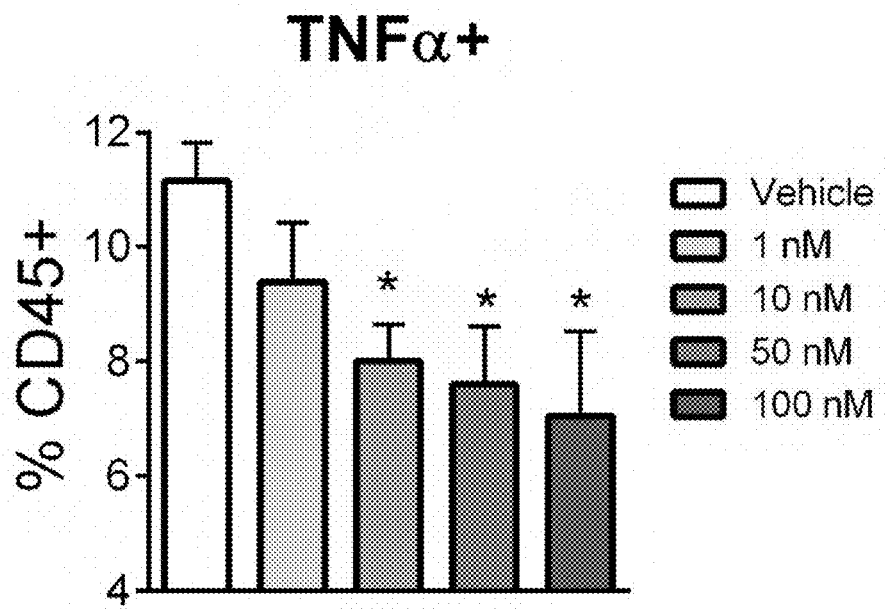
FIGS. 12A and 12B. Ex vivo translational validation of NX-13 efficacy in peripheral blood mononuclear cells (PBMCs) of ulcerative colitis patients. Flow cytometry detection of TNFα+ (FIG. 12A) and IFNγ+ (FIG. 12B) cells after ex vivo treatment with 1, 10, 50, and 100 nM of NX-13, presented as percentage of CD45+ cells. Statistical significance ($p<0.05$) is marked by asterisks.
Figure 12B:
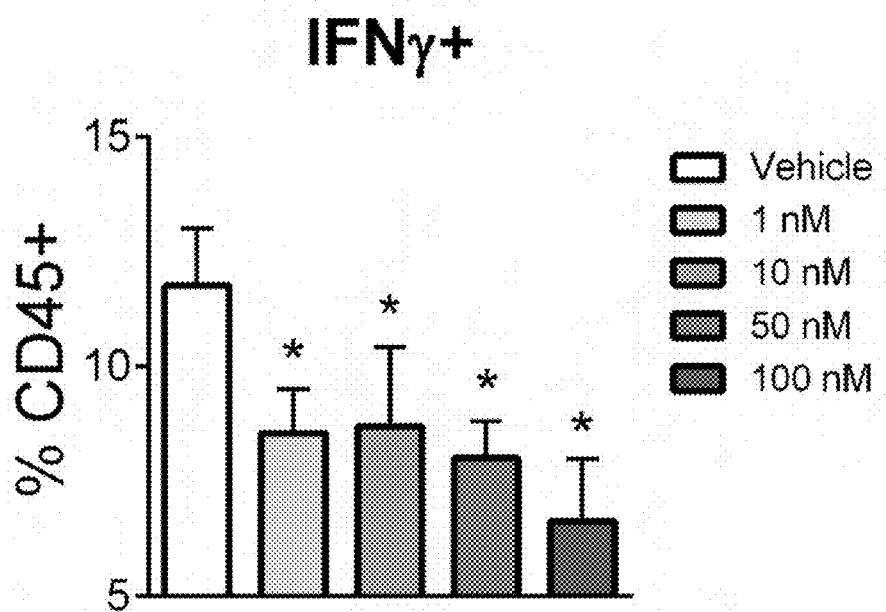

In ulcerative colitis samples, NX-13 decreased the percentage of TNFα (FIG. 12A) and IFNγ (FIG. 12B) producing CD4+ T cells, with significant reductions observed in both populations at concentrations of 10 nM and higher. While significant reductions were not observed at 1 nM in TNF, decreased trends were consistent with those observed at higher concentrations (FIG. 12A). In contrast, a significant decrease in IFNγ was observed even at 1 nM (FIG. 12B). Additionally, NX-13 reduced amount of TNFα present in each cell as measured by mean fluorescent intensity in a dose dependent manner.

Figure 13A:
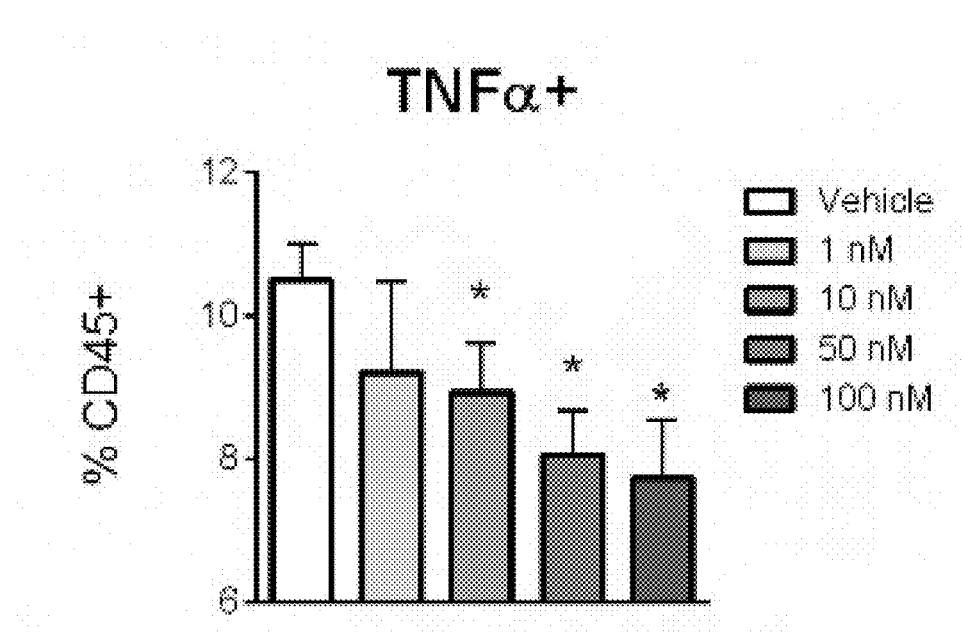
FIGS. 13A-13D. Ex vivo translational validation of NX-13 efficacy in peripheral blood mononuclear cells (PBMCs) of Crohn's disease patients. Flow cytometry detection of TNFα+ (FIG. 13A), IL4+ (FIG. 13B), IL10+ (FIG. 13C), and IFNγ+ (FIG. 13D) cells after ex vivo treatment with 1, 10, 50, and 100 nM of NX-13, presented as percentage of CD45+ cells. Statistical significance ($p<0.05$) is marked by asterisks.
Figure 13B:
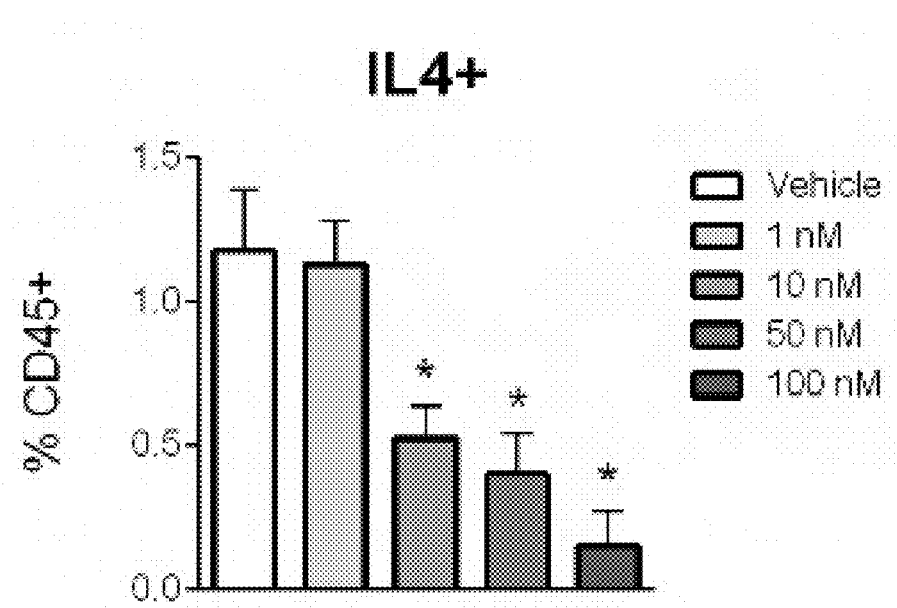
Figure 13C:
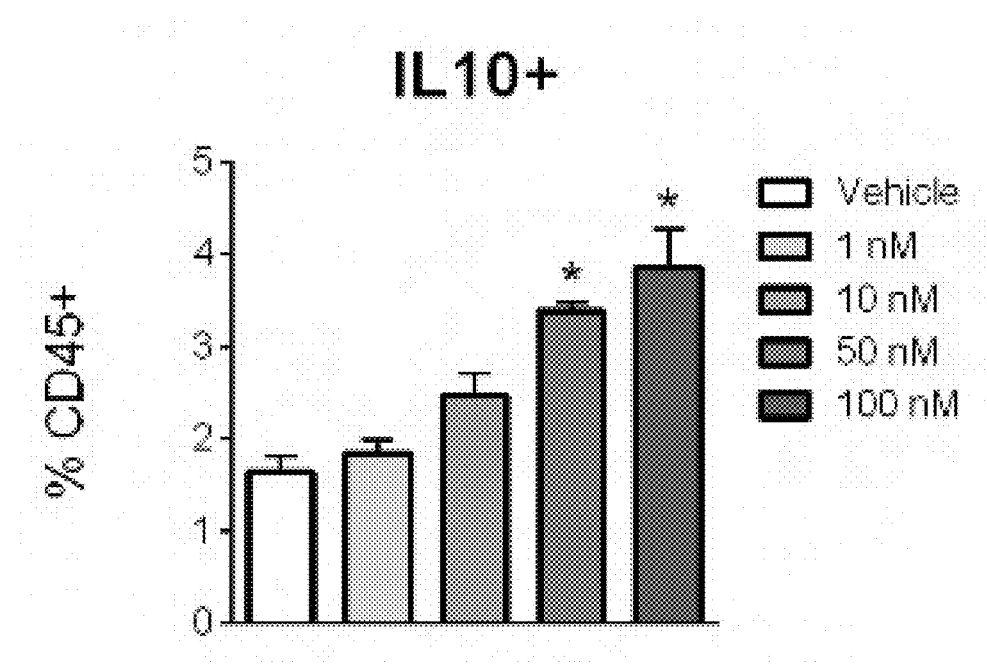
Figure 13D:
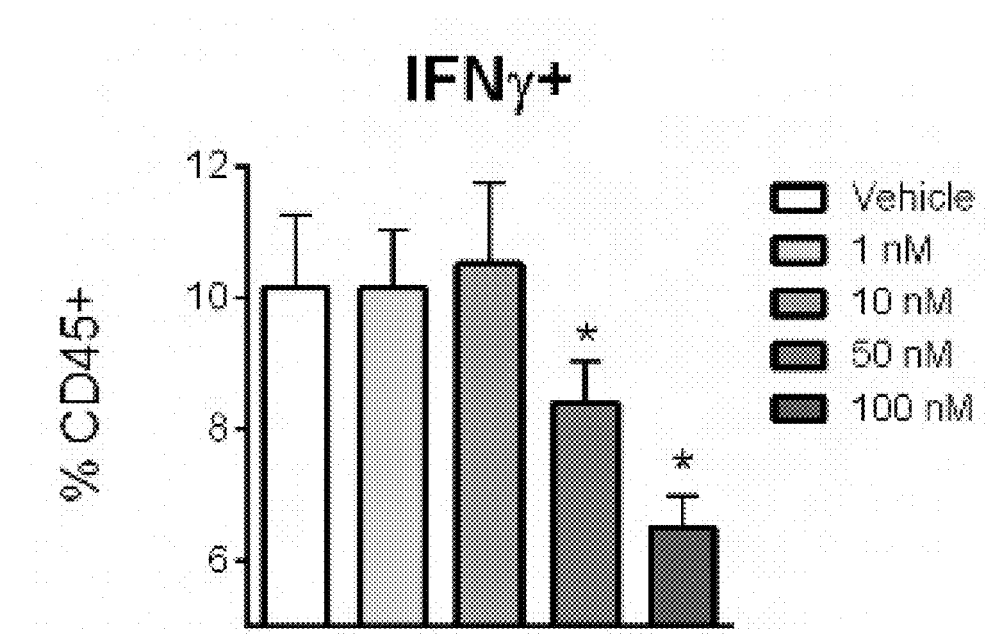

Similar to the UC tests, NX-13 potently decreased TNFα and IL-4 producing CD4+ T cells at concentrations as low as 10 nM in PBMCs from Crohn's disease patients (FIGS. 13A and 13B). Further, NX-13 treatment increased the percentage of IL10+CD4+ T cells at concentrations of 50 nM and higher (FIG. 13C), suggesting NX-13 is capable of acting in a pro-regulatory manner in addition to the direct anti-inflammatory effect on effector CD4+ T cells. Dose dependent decreases were observed in IFNγ+ cells above 50 nM NX-13 (FIG. 13D).

These results indicate that NX-13 is a viable small molecule for activating NLRX1 in human cells and for inhibition of inflammatory responses.

Example 13. Efficacy of NX-43 in a Mouse Model of Adenocarcinoma

Introduction

Ninety-five percent of colorectal cancer cases are adenocarcinomas. Adenomas or polyps, if not identified in routine colonoscopies, can spread into the intestinal wall from the epithelium and eventually metastasize after trafficking into the blood or lymph. Aside from stage 1 colon cancer which can be commonly treated by excision of a polyp or afflicted area, the five-year survival rate is bleak ranging from 63-87% for stage 2 cancers to 11% for stage 4 cancers, according to the American Cancer Society. Clear evidence has mounted that enabling factors beyond genetic instability, unlimited proliferation and apoptotic resistance are needed in the development of cancer. These factors, such as local angiogenesis, altered metabolism and immune evasion, have led to a new generation of cancer therapeutics with the ability to improve the prognosis in intermediate and advanced stages. As an immune regulator with important function in both the immune and epithelial cells of the gut, NLRX1 may serve as a potent target for the treatment of colorectal cancer.

Methods

Mouse Model.

Adult BALB/c mice were injected with $5\times10^6$ CT26 carcinoma cells subcutaneously in the hind flank. Mice were treated daily with NX-43 at 40 mg/kg via gavage beginning on day 9. Mice were weighed daily, and tumor diameter was measured every 3 days up to day 21. Tumors were collected at weighed at necropsy. A second mouse model was used. $APC^{min/+}$ mice were administered DSS in drinking water beginning at 5 weeks of age. Mice were challenged with DSS for a total of 5 days prior to return of standard drinking water. After DSS, mice were treated with NX-43 (40 mg/kg) by oral gavage for four weeks. After four weeks, colons were excised and washed. Number of polyps were counted, and colon weights were obtained.

Gene Expression.

Total RNA from tumors and lymph nodes can be generated using the Qiagen RNeasy mini kit. cDNA can be generated using the BioRad iScript cDNA synthesis kit. Standard curves can be generated by serial dilution of purified product from a standard PCR reaction with Taq DNA polymerase followed by purification using the Qiagen MinElute PCR purification kit. Expression levels can be obtained from quantitative real-time PCR with SybrGreen supermix on a BioRad CFX96 Thermal cycler followed by normalization to expression of β-actin. Gene expression can be measured for genes marking immune activation such as inflammatory cytokines or surface receptors, immune suppression such as CTLA-4, PD-1, or ARG-1, and tumor growth and metastasis.

Histopathology.

H&E stained tumor and lymph node sections can be prepared from tissue collected into 10% buffered formalin and embedded in paraffin. Slides can be examined by a board-certified veterinary pathologist via an Olympus microscope and images will be collected with Image-Pro software. Samples can be scored and evaluated for presence of tumor infiltrating leukocytes, areas of necrosis and proportion of proliferating tumor cells.

Flow Cytometry.

Tumors and lymph nodes can be collected into RPMI/FBS buffer containing collagenase (300 U/mL) and DNase (50 U/mL) for digestion. Tissues can be digested for 60 minutes under stirring at 37° C. Resultant cellular suspensions can be filtered through 100 μm strainers, centrifuged (300×g, 8 min), and washed in fresh RPMI. Following filtration of the resulting single cell suspensions, immune cells can be purified by Percoll gradient of cell-containing 40% Percoll overlayed onto 70% Percoll solution. After centrifugation, interphase can be collected and washed to obtain enriched immune cell fractions. Cells can be labeled with mixtures of extracellular (CD45, CD3, CD4, CD8, CD19, NK1.1, CD25, F4/80, CD11b, Gr1, CX3CR1, CD64, CD40, CTLA4) and intracellular (Tbet, RORγT, FOXP3, IFNγ, IL17, IL10, granzyme B, iNOS) antibodies in a sequential live staining in 96-well plates. Data can be acquired using a FACS Celesta flow cytometer with FACSDiva software.

Results

Figure 14A:
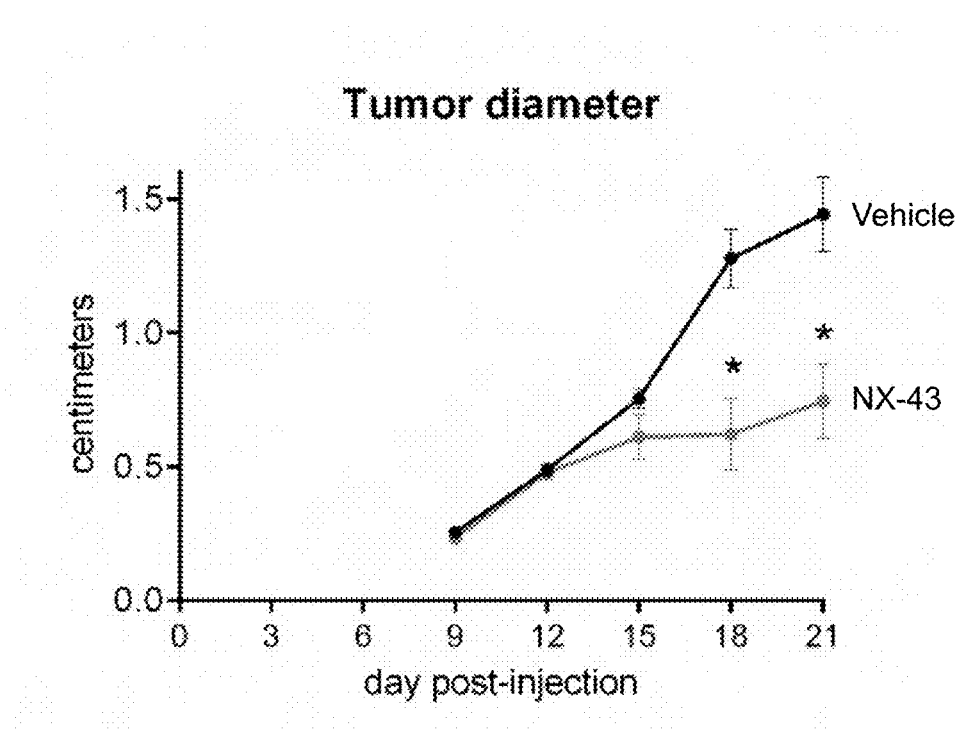
FIGS. 14A and 14B. Efficacy of NX-43 in a CT26 injected solid tumor model. Tumor size by diameter (FIG. 14A) and mass (FIG. 14B) after treatment with NX-43 (40 mg/kg) beginning 9 days post-injection of CT26 cells. Statistical significance ($p<0.05$) is marked by asterisks.
Figure 14B:
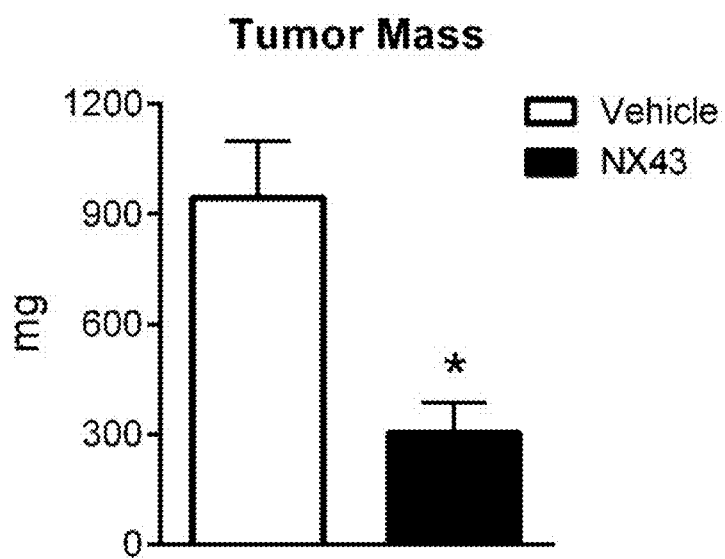
Figure 15A:
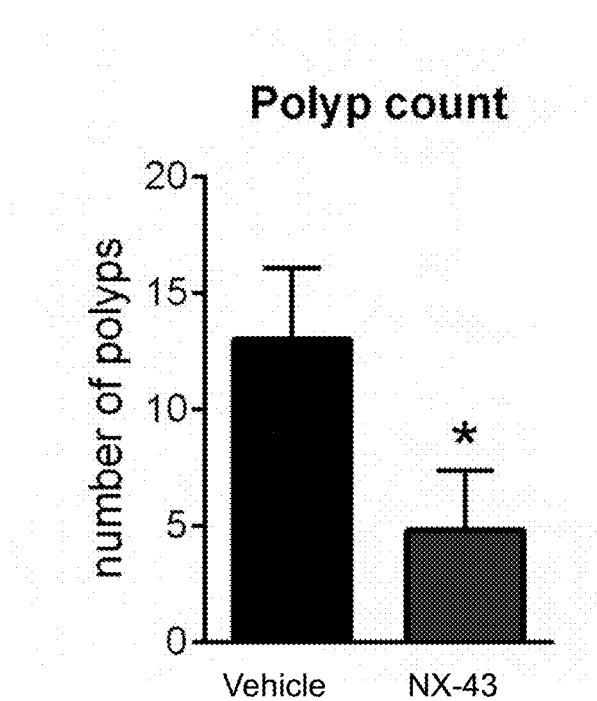
FIGS. 15A and 15B. Efficacy of NX-43 in an $APC^{min/+}$ model of colorectal cancer. Number of colonic polyps (FIG. 15A) and colon weight (FIG. 15B) after four weeks of treatment with NX-43 (40 mg/kg, oral). Statistical significance ($p<0.05$) is marked by asterisks.
Figure 15B:
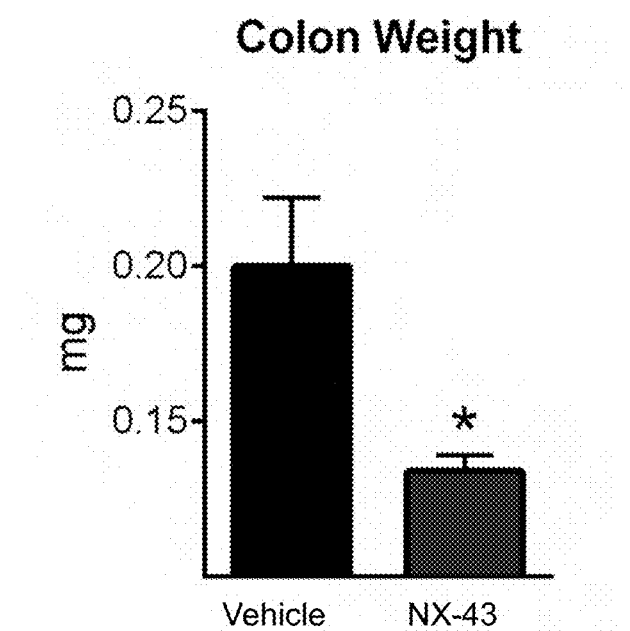

The CT26 solid tumor model is a highly immunogenic model of carcinoma, making it a valuable model in the evaluation of novel therapeutics. NLRX1 inhibitors, such as NX-43, reduce tumor size relative to untreated controls (FIGS. 14A and 14B). Significantly, reduction in tumor diameter was observed in less than 10 days after initiation of NX-43 treatment. Meanwhile, after 12 days of treatment, the overall tumor mass was observed to be reduced by over 70%. In the $APC^{min/+}$ model of colorectal cancer (FIGS. 15A and 15B), post-inflammation treatment with NX-43 reduced the number of colonic polyps and the overall tumor burden (as evidenced by the colon weight). Histologically, these effects are expected to correlate with increased proportions of tumor infiltrating leukocytes. The expression of immune activating genes is expected to rise while suppressive genes are expected to be downregulated. By flow cytometry, numbers of suppressive cell types, such as Tregs or myeloid derived suppressor cells, are expected to decrease, and number of activated cytotoxic T cells and granzyme B+ cells are predicted to increase.

Example 14. Efficacy of NX-43 in a Model Viral Infection

Introduction

As a sensor of viral nucleic acid and a modulator of MAVS and STING pathways, NLRX1 is central to the response to viruses. Indeed, the importance of NLRX1 in the native viral response has been identified in models of influenza, hepatitis C, HIV, and herpes virus [7, 9, 12, 14]. While the intricacies of the overall immune response vary between viruses, it is clear that NLRX1-mediated mechanisms are present in each with downstream effects on expression of type I interferons and viral clearance. In this, the inhibition of NLRX1 by specific inhibitors may activate the immune response, prevent the host evasion and immunosuppression and initiate pathways of viral clearance. To validate the efficacy of NX-43, we will use a mouse model of influenza virus infection.

Methods

Mouse Model.

Eight- to ten-week old wild type C57BL/6 mice will be anesthetized by isoflurane inhalation. Mice will be infected with influenza A (H1N1) intranasally at a challenge titer of 350 pfu/mouse [37]. Mice will be treated daily with NX-43 at doses of 10, 20 and 40 mg/kg either orally via gavage or intravenously by tail vein injection. Mice will be weighed and scored daily over 14 days. Mice will be euthanized at days 3, 7, 11 and 14 to measure titers of virus within the lung and generation of immune responses by gene expression and flow cytometry.

Viral Titer.

Lung homogenates will be prepared from untreated and NX-43 treated mice. MDCK cells will be grown to confluency within six-well plates. Cells will be washed of serum containing media prior to exposure. Serial dilutions of virus sample will be made in serum-free growth media containing fraction V BSA. Cells will be incubated with 1 mL of virus dilution for 1 h at 37° C. Supernatant will be removed and cells will be washed. Cells will be overlayed with a MEM agar mixture and incubated for 72 h. Overlay will be removed, and wells will be stained with crystal violet. Lowest dilution with at least 50 plaques will be counted.

Gene Expression.

Total RNA from the lung will be generated using the Qiagen RNeasy mini kit. cDNA will be generated using the BioRad iScript cDNA synthesis kit. Standard curves will be generated by serial dilution of purified product from a standard PCR reaction with Taq DNA polymerase followed by purification using the Qiagen MinElute PCR purification kit. Expression levels will be obtained from quantitative real-time PCR with SybrGreen supermix on a BioRad CFX96 Thermal cycler followed by normalization to expression of $\beta$-actin. Gene expression will be measured for IL-6, interferon-alpha, interferon-beta, Stat2, Oas1a, RIG-I, and MAVS.

Flow Cytometry.

Lungs will be chopped into small pieces and collected into RPMI/FBS/CaCl$_2$ buffer containing collagenase (300 U/mL) and DNase (50 U/mL) for digestion. Tissues will be digested for 60 to 90 minutes under stirring at 37° C. Resultant cellular suspensions will be filtered through 100 µm strainers, centrifuged (300×g, 8 min), and washed in fresh RPMI. Red blood cells will be lysed by hypotonic lysis and removed by filtration. Cells will be washed and plated for flow cytometry staining. Cells will be labeled with mixtures of extracellular (CD45, CD3, CD4, CD8, CD19, NK1.1, CD25, F4/80, CD11b, CD11c, Gr1, CX3CR1, CD64, SiglecF, Ly6C) and intracellular (Tbet, RORγT, FOXP3, IFNγ, IL6, IL10, IFNb) antibodies in a sequential live staining in 96-well plates. Data will be acquired using a FACS Celesta flow cytometer with FACSDiva software.

Results

Primary efficacy of NX-43 in this model of influenza A infection will be the evaluation of viral titers. With the inhibition of NLRX1, greater immune activation and interferon responses are predicted, which is predicted to reduce the level of virus in the lungs and provide clearance earlier than in untreated mice. As stated, this clearance is predicted to be enabled by increased expression of type 1 interferons and inflammatory cytokines such as IL-6. The facilitated clearance of virus is predicted to result in faster recovery of weight after the initial phase of the infection. The activated immune response is predicted to result in higher percentages of inflammatory T cells, macrophages and neutrophils in the lungs during infection.

REFERENCES

1. Davis, B. K., et al., *Emerging significance of NLRs in inflammatory bowel disease.* Inflamm Bowel Dis, 2014. 20(12): p. 2412-32.
2. Arnoult, D., et al., *An N-terminal addressing sequence targets NLRX1 to the mitochondrial matrix.* J Cell Sci, 2009. 122(Pt 17): p. 3161-8.
3. Leber, A., et al., *NLRX1 Regulates Effector and Metabolic Functions of CD4+ T Cells.* J Immunol, 2017.
4. Leber, A., et al., *NLRX1 Modulates Immunometabolic Mechanisms Controlling the Host-Gut Microbiota Interactions during Inflammatory Bowel Disease.* Front Immunol, 2018. 9: p. 363.
5. Lu, P., et al., *Modeling-Enabled Characterization of Novel NLRX1 Ligands.* PLoS One, 2015. 10(12): p. e0145420.
6. Soares, F., et al., *The mitochondrial protein NLRX1 controls the balance between extrinsic and intrinsic apoptosis.* J Biol Chem, 2014. 289(28): p. 19317-30.
7. Allen, I. C., et al., *NLRX1 protein attenuates inflammatory responses to infection by interfering with the RIG-I-MAVS and TRAF6-NF-kappaB signaling pathways.* Immunity, 2011. 34(6): p. 854-65.
8. Feng, H., et al., *NLRX1 promotes immediate IRF1-directed antiviral responses by limiting dsRNA-activated translational inhibition mediated by PKR.* Nat Immunol, 2017. 18(12): p. 1299-1309.
9. Guo, H., et al., *NLRX1 Sequesters STING to Negatively Regulate the Interferon Response, Thereby Facilitating the Replication of HIV-1 and DNA Viruses.* Cell Host Microbe, 2016. 19(4): p. 515-528.
10. Jaworska, J., et al., *NLRX1 prevents mitochondrial induced apoptosis and enhances macrophage antiviral immunity by interacting with influenza virus PB1-F2 protein.* Proc Natl Acad Sci USA, 2014. 111(20): p. E2110-9.
11. Kim, J. H., et al., *FAS-associated factor-1 positively regulates type I interferon response to RNA virus infection by targeting NLRX1.* PLoS Pathog, 2017. 13(5): p. e1006398.
12. Ma, Z., et al., *NLRX1 negatively modulates type I IFN to facilitate KSHV reactivation from latency.* PLoS Pathog, 2017. 13(5): p. e1006350.
13. Moore, C. B., et al., *NLRX1 is a regulator of mitochondrial antiviral immunity.* Nature, 2008. 451(7178): p. 573-7.

14. Qin, Y., et al., *NLRX1 mediates MAVS degradation to attenuate hepatitis C virus-induced innate immune response through PCBP2*. J Virol, 2017.
15. Philipson, C. W., et al., *Modeling the Regulatory Mechanisms by Which NLRX1 Modulates Innate Immune Responses to Helicobacter pylori Infection*. PLoS One, 2015. 10(9): p. e0137839.
16. Kale, S. D., et al., *Modulation of Immune Signaling and Metabolism Highlights Host and Fungal Transcriptional Responses in Mouse Models of Invasive Pulmonary Aspergillosis*. Sci Rep, 2017. 7(1): p. 17096.
17. Coutermarsh-Ott, S., et al., *NLRX1 suppresses tumorigenesis and attenuates histiocytic sarcoma through the negative regulation of NF-kappaB signaling*. Oncotarget, 2016. 7(22): p. 33096-110.
18. Koblansky, A. A., et al., *The Innate Immune Receptor NLRX1 Functions as a Tumor Suppressor by Reducing Colon Tumorigenesis and Key Tumor-Promoting Signals*. Cell Rep, 2016. 14(11): p. 2562-75.
19. Lei, Y., et al., *EGFR-targeted mAb therapy modulates autophagy in head and neck squamous cell carcinoma through NLRX1-TUFM protein complex*. Oncogene, 2016. 35(36): p. 4698-707.
20. Singh, K., et al., *NLRX1 acts as tumor suppressor by regulating TNF-alpha induced apoptosis and metabolism in cancer cells*. Biochim Biophys Acta, 2015. 1853(5): p. 1073-86.
21. Tattoli, I., et al., *NLRX1 Acts as an Epithelial-Intrinsic Tumor Suppressor through the Modulation of TNF-Mediated Proliferation*. Cell Rep, 2016. 14(11): p. 2576-86.
22. Kors, L., et al., *Deletion of NLRX1 increases fatty acid metabolism and prevents diet-induced hepatic steatosis and metabolic syndrome*. Biochim Biophys Acta, 2018. 1864(5 Pt A): p. 1883-1895.
23. Wang, Y. G., et al., *The involvement of NLRX1 and NLRP3 in the development of nonalcoholic steatohepatitis in mice*. J Chin Med Assoc, 2013. 76(12): p. 686-92.
24. Costford, S. R., et al., *Male Mice Lacking NLRX1 Are Partially Protected From High-Fat Diet-Induced Hyperglycemia*. J Endocr Soc, 2018. 2(4): p. 336-347.
25. Theus, M. H., et al., *Loss of NLRX1 Exacerbates Neural Tissue Damage and NF-kappaB Signaling following Brain Injury*. J Immunol, 2017. 199(10): p. 3547-3558.
26. Li, H., et al., *NLRX1 attenuates apoptosis and inflammatory responses in myocardial ischemia by inhibiting MAVS-dependent NLRP3 inflammasome activation*. Mol Immunol, 2016. 76: p. 90-7.
27. Kang, M. J., et al., *Suppression of NLRX1 in chronic obstructive pulmonary disease*. J Clin Invest, 2015. 125 (6): p. 2458-62.
28. Eitas, T. K., et al., *The nucleotide-binding leucine-rich repeat (NLR) family member NLRX1 mediates protection against experimental autoimmune encephalomyelitis and represses macrophage/microglia-induced inflammation*. J Biol Chem, 2014. 289(7): p. 4173-9.
29. Hong, M., S. I. Yoon, and I. A. Wilson, *Structure and functional characterization of the RNA-binding element of the NLRX1 innate immune modulator*. Immunity, 2012. 36(3): p. 337-47.
30. Finn, O. J., *Immuno-oncology: understanding the function and dysfunction of the immune system in cancer*. Ann Oncol, 2012. 23 Suppl 8: p. viii 6-9.
31. Abreu, M. T., *Toll-like receptor signalling in the intestinal epithelium: how bacterial recognition shapes intestinal function*. Nat Rev Immunol, 2010. 10(2): p. 131-44.
32. Baumgart, D. C. and W. J. Sandborn, *Crohn's disease*. Lancet, 2012. 380(9853): p. 1590-605.
33. Sartor, R. B., *Mechanisms of disease: pathogenesis of Crohn's disease and ulcerative colitis*. Nat Clin Pract Gastroenterol Hepatol, 2006. 3(7): p. 390-407.
34. Haarberg, K. M., et al., *Orally administered extract from Prunella vulgaris attenuates spontaneous colitis in mdr1a (-/-) mice*. World J Gastrointest Pharmacol Ther, 2015. 6(4): p. 223-37.
35. Leber, A., et al., *Activation of LANCL2 by BT-11 Ameliorates IBD by Supporting Regulatory T Cell Stability Through Immunometabolic Mechanisms*. Inflamm Bowel Dis, 2018.
36. Schwab, M., et al., *Association between the C3435T MDR1 gene polymorphism and susceptibility for ulcerative colitis*. Gastroenterology, 2003. 124(1): p. 26-33.
37. Leber, A., et al., *Lanthionine Synthetase C-Like 2 Modulates Immune Responses to Influenza Virus Infection*. Front Immunol, 2017. 8: p. 178.

We claim:

1. A compound having the structure of:

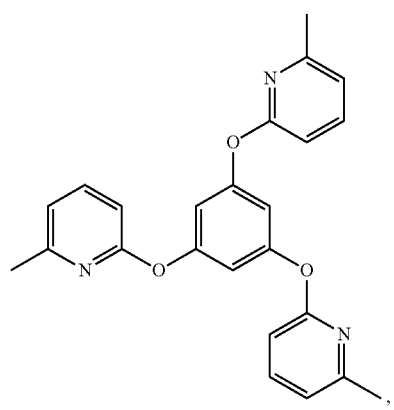

or a salt thereof.